United States Patent
Al-Ali et al.

(10) Patent No.: US 11,191,485 B2
(45) Date of Patent: *Dec. 7, 2021

(54) PARAMETER UPGRADE SYSTEM

(71) Applicant: Masimo Corporation, Irvine, CA (US)

(72) Inventors: Ammar Al-Ali, San Juan Capistrano, CA (US); Philip B. Trinh, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 394 days.

This patent is subject to a terminal disclaimer.

(21) Appl. No.: 16/247,316

(22) Filed: Jan. 14, 2019

(65) Prior Publication Data

US 2019/0216398 A1 Jul. 18, 2019

Related U.S. Application Data

(63) Continuation of application No. 11/757,925, filed on Jun. 4, 2007, now Pat. No. 10,188,348.

(Continued)

(51) Int. Cl.
*A61B 5/00* (2006.01)
*A61B 5/1455* (2006.01)
(Continued)

(52) U.S. Cl.
CPC ........ *A61B 5/6838* (2013.01); *A61B 5/14551* (2013.01); *A61B 5/6826* (2013.01); *G16H 40/40* (2018.01); *G16Z 99/00* (2019.02); *A61B 2562/08* (2013.01); *G05B 2219/23308* (2013.01); *G05B 2219/23339* (2013.01)

(58) Field of Classification Search
None
See application file for complete search history.

(56) References Cited

U.S. PATENT DOCUMENTS 2,567,926 A 9/1951 Dunkelberger
3,103,214 A 9/1963 Smith
(Continued)

FOREIGN PATENT DOCUMENTS

AU 8593891 4/1992
CA 2052650 4/1992
(Continued)

OTHER PUBLICATIONS

US 8,845,543 B2, 09/2014, Diab et al. (withdrawn)
(Continued)

*Primary Examiner* — Shirley X Jian
(74) *Attorney, Agent, or Firm* — Knobbe, Martens, Olson & Bear, LLP

(57) ABSTRACT

A physiological monitor has a sensor port configured to attach and communicate with a sensor. A processor board is in communications with the sensor port and has a board digital signal processor (DSP). Firmware residing on the processor board is executable by the board DSP so as to calculate physiological parameters in response to a sensor signal received from the sensor. Upgrade tools are individually attachable to the sensor port in lieu of the sensor so as to designate to the processor board which of the physiological parameters, if any, to calculate when the sensor is attached to the sensor port.

17 Claims, 15 Drawing Sheets

Related U.S. Application Data

(60) Provisional application No. 60/811,001, filed on Jun. 5, 2006.

(51) Int. Cl.
  *G16H 40/40* (2018.01)
  *G16Z 99/00* (2019.01)

(56) References Cited

U.S. PATENT DOCUMENTS

| | | |
|---|---|---|
| 3,313,290 A | 4/1967 | Chance et al. |
| 3,319,216 A | 5/1967 | McCullough |
| 3,463,142 A | 8/1969 | Harte et al. |
| 3,482,565 A | 12/1969 | Gowen |
| 3,543,310 A | 10/1970 | Pelissier |
| 3,647,299 A | 3/1972 | Lavallee |
| 3,704,706 A | 12/1972 | Herczfeld et al. |
| 3,710,303 A | 1/1973 | Gallagher, Jr. |
| 3,711,272 A | 1/1973 | Randall et al. |
| 3,740,570 A | 6/1973 | Kaelin et al. |
| 3,799,672 A | 3/1974 | Vurek |
| 3,802,776 A | 4/1974 | Tchang |
| 3,970,353 A | 7/1976 | Kaufman |
| 3,995,209 A | 11/1976 | Weston |
| 4,051,522 A | 9/1977 | Healy et al. |
| 4,086,915 A | 5/1978 | Kofsky et al. |
| 4,129,124 A | 12/1978 | Thalmann |
| 4,169,976 A | 10/1979 | Cirri |
| 4,182,977 A | 1/1980 | Stricklin, Jr. |
| 4,216,462 A | 8/1980 | McGrath et al. |
| 4,237,344 A | 12/1980 | Moore |
| 4,305,401 A | 12/1981 | Reissmueller et al. |
| 4,308,456 A | 12/1981 | Van Der Gaag et al. |
| 4,321,930 A | 3/1982 | Jobsis et al. |
| 4,334,544 A | 6/1982 | Hill et al. |
| 4,346,590 A | 8/1982 | Brown |
| 4,350,165 A | 9/1982 | Striese |
| 4,356,475 A | 10/1982 | Neumann et al. |
| 4,380,240 A | 4/1983 | Jöbsis et al. |
| 4,406,289 A | 9/1983 | Wesseling et al. |
| 4,407,290 A | 10/1983 | Wilber |
| 4,414,980 A | 11/1983 | Mott |
| 4,449,821 A | 5/1984 | Lee |
| 4,451,694 A | 5/1984 | Harper et al. |
| 4,480,886 A | 11/1984 | Bergamin |
| 4,481,804 A | 11/1984 | Eberhard et al. |
| 4,490,003 A | 12/1984 | Robinson |
| 4,498,722 A | 2/1985 | Fedder et al. |
| 4,505,848 A | 3/1985 | Kobayashi |
| 4,528,986 A | 7/1985 | Arundel et al. |
| 4,531,795 A | 7/1985 | Sinclair |
| 4,580,867 A | 4/1986 | Wright et al. |
| 4,621,643 A | 11/1986 | New, Jr. et al. |
| 4,636,786 A | 1/1987 | Haertling |
| 4,642,627 A | 2/1987 | Hodsdon |
| 4,648,028 A | 3/1987 | DeKlotz |
| 4,653,498 A | 3/1987 | New, Jr. et al. |
| 4,674,085 A | 6/1987 | Aranguren et al. |
| 4,684,245 A | 8/1987 | Goldring |
| 4,684,246 A | 8/1987 | Downing et al. |
| 4,685,464 A | 8/1987 | Goldberger et al. |
| 4,690,492 A | 9/1987 | Beard |
| 4,695,258 A | 9/1987 | Hanson et al. |
| 4,700,708 A | 10/1987 | New, Jr. et al. |
| 4,770,179 A | 9/1988 | New, Jr. et al. |
| 4,797,125 A | 1/1989 | Malana |
| 4,815,469 A | 3/1989 | Cohen et al. |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,834,532 A | 5/1989 | Yount |
| 4,838,808 A | 6/1989 | Fujiura |
| 4,843,013 A | 6/1989 | Chiang |
| 4,844,784 A | 7/1989 | Suzuki et al. |
| 4,848,901 A | 7/1989 | Hood, Jr. |
| 4,858,615 A | 8/1989 | Meinema |
| 4,859,057 A | 8/1989 | Taylor et al. |
| 4,865,038 A | 9/1989 | Rich et al. |
| 4,867,165 A | 9/1989 | Noller et al. |
| 4,877,322 A | 10/1989 | Hill |
| 4,880,304 A | 11/1989 | Jaeb et al. |
| 4,887,260 A | 12/1989 | Carden et al. |
| 4,900,904 A | 2/1990 | Wright et al. |
| 4,907,594 A | 3/1990 | Muz |
| 4,913,150 A | 4/1990 | Cheung et al. |
| 4,916,444 A | 4/1990 | King |
| 4,920,339 A | 4/1990 | Friend et al. |
| 4,927,264 A | 5/1990 | Shiga et al. |
| 4,938,218 A | 7/1990 | Goodman et al. |
| 4,942,877 A | 7/1990 | Sakai et al. |
| 4,952,177 A | 8/1990 | Drake et al. |
| 4,960,128 A | 10/1990 | Gordon et al. |
| 4,961,711 A | 10/1990 | Fujiura et al. |
| 4,964,408 A | 10/1990 | Hink et al. |
| 4,974,591 A | 12/1990 | Awazu et al. |
| 4,996,975 A | 3/1991 | Nakamura |
| 5,007,704 A | 4/1991 | McCartney |
| RE33,643 E | 7/1991 | Isaacson et al. |
| 5,031,608 A | 7/1991 | Weinstein |
| 5,038,800 A | 8/1991 | Oba |
| 5,041,187 A | 8/1991 | Hink et al. |
| 5,058,098 A | 10/1991 | Sakaue et al. |
| 5,058,588 A | 10/1991 | Kaestle |
| 5,061,916 A | 10/1991 | French et al. |
| 5,066,859 A | 11/1991 | Karkar et al. |
| 5,069,213 A | 12/1991 | Polczynski |
| 5,080,098 A | 1/1992 | Willett et al. |
| 5,086,229 A | 2/1992 | Rosenthal et al. |
| 5,087,242 A | 2/1992 | Petelenz et al. |
| 5,090,410 A | 2/1992 | Saper et al. |
| 5,099,842 A | 3/1992 | Mannheimer et al. |
| 5,108,298 A | 4/1992 | Simmel |
| 5,109,848 A | 5/1992 | Thomas et al. |
| 5,109,849 A | 5/1992 | Goodman et al. |
| 5,113,862 A | 5/1992 | Mortazavi |
| 5,125,403 A | 6/1992 | Culp |
| 5,126,648 A | 6/1992 | Jacobs |
| 5,140,228 A | 8/1992 | Biegel |
| 5,158,323 A | 10/1992 | Yamamoto et al. |
| 5,163,438 A | 11/1992 | Gordon et al. |
| 5,170,786 A | 12/1992 | Thomas et al. |
| 5,188,098 A | 2/1993 | Hoffman et al. |
| 5,193,543 A | 3/1993 | Yelderman |
| 5,209,230 A | 5/1993 | Swedlow et al. |
| 5,217,013 A | 6/1993 | Lewis et al. |
| 5,224,478 A | 7/1993 | Sakai et al. |
| 5,224,882 A | 7/1993 | Olms |
| 5,246,003 A | 9/1993 | DeLonzor |
| 5,247,931 A | 9/1993 | Norwood |
| 5,249,576 A | 10/1993 | Goldberger et al. |
| 5,266,792 A | 11/1993 | Crowne et al. |
| 5,267,562 A | 12/1993 | Ukawa et al. |
| 5,287,853 A | 2/1994 | Vester et al. |
| 5,295,852 A | 3/1994 | Renn et al. |
| 5,295,872 A | 3/1994 | Christensson |
| 5,297,548 A | 3/1994 | Pologe |
| 5,302,133 A | 4/1994 | Tondreault |
| 5,308,919 A | 5/1994 | Minnich |
| 5,309,908 A | 5/1994 | Friedman et al. |
| 5,313,940 A | 5/1994 | Fuse et al. |
| 5,317,269 A | 5/1994 | Mills et al. |
| 5,319,355 A | 6/1994 | Russek |
| 5,319,363 A | 6/1994 | Welch et al. |
| 5,337,744 A | 8/1994 | Branigan |
| 5,339,810 A | 8/1994 | Ivers et al. |
| 5,341,805 A | 8/1994 | Stavridi et al. |
| 5,365,937 A | 11/1994 | Reeves et al. |
| D353,195 S | 12/1994 | Savage et al. |
| D353,196 S | 12/1994 | Savage et al. |
| 5,377,676 A | 1/1995 | Vari et al. |
| 5,380,213 A | 1/1995 | Piorunneck et al. |
| 5,387,122 A | 2/1995 | Goldberger et al. |
| 5,390,670 A | 2/1995 | Centa et al. |

(56) References Cited

U.S. PATENT DOCUMENTS

| | | |
|---|---|---|
| 5,397,247 A | 3/1995 | Aoki et al. |
| 5,400,267 A | 3/1995 | Denen et al. |
| 5,407,368 A | 4/1995 | Strand et al. |
| 5,415,629 A | 5/1995 | Henley |
| D359,546 S | 6/1995 | Savage et al. |
| 5,422,632 A | 6/1995 | Bucholtz et al. |
| 5,425,375 A | 6/1995 | Chin et al. |
| 5,431,170 A | 7/1995 | Mathews |
| 5,436,499 A | 7/1995 | Namavar et al. |
| D361,840 S | 8/1995 | Savage et al. |
| 5,438,986 A | 8/1995 | Disch et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,460,182 A | 10/1995 | Goodman et al. |
| 5,469,845 A | 11/1995 | DeLonzor et al. |
| 5,479,934 A | 1/1996 | Imran |
| 5,482,036 A | 1/1996 | Diab et al. |
| 5,490,505 A | 2/1996 | Diab et al. |
| 5,490,523 A | 2/1996 | Isaacson et al. |
| 5,494,043 A | 2/1996 | O'Sullivan et al. |
| 5,498,235 A | 3/1996 | Flower |
| 5,509,823 A | 4/1996 | Harting et al. |
| 5,515,169 A | 5/1996 | Cargill et al. |
| 5,520,177 A | 5/1996 | Ogawa et al. |
| 5,521,997 A | 5/1996 | Rovenolt et al. |
| 5,533,509 A | 7/1996 | Koashi et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,564,108 A | 10/1996 | Hunsaker et al. |
| 5,564,417 A | 10/1996 | Chance |
| 5,569,823 A | 10/1996 | Schreier et al. |
| 5,570,002 A | 10/1996 | Castleman |
| 5,575,284 A | 11/1996 | Athan et al. |
| 5,579,001 A | 11/1996 | Dempsey et al. |
| 5,579,775 A | 12/1996 | Dempsey et al. |
| 5,584,296 A | 12/1996 | Cui et al. |
| 5,588,427 A | 12/1996 | Tien |
| 5,590,649 A | 1/1997 | Caro et al. |
| 5,602,924 A | 2/1997 | Durand et al. |
| 5,617,857 A | 4/1997 | Chader et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,671,914 A | 9/1997 | Kalkhoran et al. |
| 5,673,693 A | 10/1997 | Solenberger |
| 5,678,544 A | 10/1997 | DeLonzor et al. |
| 5,682,803 A | 11/1997 | Boianjlu |
| 5,685,299 A | 11/1997 | Diab et al. |
| 5,687,734 A | 11/1997 | Dempsey et al. |
| 5,692,503 A | 12/1997 | Kuenstner |
| 5,715,390 A | 2/1998 | Hoffman |
| 5,720,293 A | 2/1998 | Quinn et al. |
| 5,726,440 A | 3/1998 | Kalkhoran et al. |
| D393,830 S | 4/1998 | Tobler et al. |
| 5,742,512 A | 4/1998 | Edge |
| 5,743,262 A | 4/1998 | Lepper, Jr. et al. |
| 5,747,806 A | 5/1998 | Khalil et al. |
| 5,748,103 A | 5/1998 | Flach et al. |
| 5,750,994 A | 5/1998 | Schlager |
| 5,758,644 A | 6/1998 | Diab et al. |
| 5,760,910 A | 6/1998 | Lepper, Jr. et al. |
| 5,767,791 A | 6/1998 | Stoop et al. |
| 5,769,785 A | 6/1998 | Diab et al. |
| 5,770,028 A | 6/1998 | Maley et al. |
| 5,779,630 A | 7/1998 | Fein et al. |
| 5,782,757 A | 7/1998 | Diab et al. |
| 5,785,644 A | 7/1998 | Diab et al. |
| 5,785,659 A | 7/1998 | Caro et al. |
| 5,790,432 A | 8/1998 | Morys |
| 5,791,347 A | 8/1998 | Flaherty et al. |
| 5,803,909 A | 9/1998 | Maki et al. |
| 5,807,247 A | 9/1998 | Mechant et al. |
| 5,807,248 A | 9/1998 | Mills |
| 5,810,724 A | 9/1998 | Gronvall |
| 5,810,734 A | 9/1998 | Caro et al. |
| 5,817,010 A | 10/1998 | Hibi |
| 5,818,985 A | 10/1998 | Merchant et al. |
| 5,823,950 A | 10/1998 | Diab et al. |
| 5,830,129 A | 11/1998 | Baer et al. |
| 5,830,131 A | 11/1998 | Caro et al. |
| 5,833,618 A | 11/1998 | Caro et al. |
| 5,841,435 A | 11/1998 | Dauerer et al. |
| 5,860,919 A | 1/1999 | Kiani-Azarbayjany et al. |
| 5,890,929 A | 4/1999 | Mills et al. |
| 5,895,369 A | 4/1999 | Flower |
| 5,904,654 A | 5/1999 | Wohltmann et al. |
| 5,919,133 A | 7/1999 | Taylor et al. |
| 5,919,134 A | 7/1999 | Diab |
| 5,934,925 A | 8/1999 | Tobler et al. |
| 5,939,609 A | 8/1999 | Knapp et al. |
| 5,940,182 A | 8/1999 | Lepper, Jr. et al. |
| 5,957,885 A | 9/1999 | Bollish et al. |
| 5,970,353 A | 10/1999 | Sultan |
| 5,987,343 A | 11/1999 | Kinast |
| 5,991,355 A | 11/1999 | Dahlke |
| 5,995,855 A | 11/1999 | Kiani et al. |
| 5,997,343 A | 12/1999 | Mills et al. |
| 5,999,834 A | 12/1999 | Wang et al. |
| 6,002,952 A | 12/1999 | Diab et al. |
| 6,010,937 A | 1/2000 | Karam et al. |
| 6,011,985 A | 1/2000 | Athan et al. |
| 6,011,986 A | 1/2000 | Diab et al. |
| 6,014,576 A | 1/2000 | Raley |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,061,584 A | 5/2000 | Lovejoy et al. |
| 6,066,204 A | 5/2000 | Haven |
| 6,067,462 A | 5/2000 | Diab et al. |
| 6,074,345 A | 6/2000 | van Oostrom et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,174,283 B1 | 1/2001 | Nevo |
| 6,184,521 B1 | 2/2001 | Coffin, IV et al. |
| 6,206,830 B1 | 3/2001 | Diab et al. |
| 6,223,064 B1 | 4/2001 | Lynn et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,268,283 B1 | 7/2001 | Huang |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,282,438 B1 | 8/2001 | Maki et al. |
| 6,285,896 B1 | 9/2001 | Tobler et al. |
| 6,301,493 B1 | 10/2001 | Marro et al. |
| 6,308,089 B1 | 10/2001 | Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,330,468 B1 | 12/2001 | Scharf |
| 6,334,065 B1 | 12/2001 | Al-Ali et al. |

(56) References Cited

U.S. PATENT DOCUMENTS

| | | |
|---|---|---|
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,433,696 B1 | 8/2002 | Deiterman et al. |
| 6,440,067 B1 | 8/2002 | DeLuca et al. |
| 6,463,142 B1 | 10/2002 | Kilp |
| 6,463,311 B1 | 10/2002 | Diab |
| 6,470,199 B1 | 10/2002 | Kopotic et al. |
| 6,473,632 B1 | 10/2002 | Myers |
| 6,487,429 B2 | 11/2002 | Hockersmith et al. |
| 6,496,711 B1 | 12/2002 | Athan et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,553,241 B2 | 4/2003 | Mannheimer et al. |
| 6,558,276 B1 | 5/2003 | Yokota et al. |
| 6,571,113 B1 | 5/2003 | Fein et al. |
| 6,580,086 B1 | 6/2003 | Schulz et al. |
| 6,584,336 B1 | 6/2003 | Al-Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,511 B1 | 8/2003 | Ali et al. |
| 6,611,320 B1 | 8/2003 | Lindberg et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,728,561 B2 | 4/2004 | Smith et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,763,256 B2 | 7/2004 | Kimball et al. |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,790,178 B1 | 9/2004 | Mault et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,879,850 B2 | 4/2005 | Kimball |
| 6,898,452 B2 | 5/2005 | Al-Ali et al. |
| 6,920,345 B2 | 7/2005 | Al-Ali et al. |
| 6,928,370 B2 | 8/2005 | Anuzis et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,763 B2 | 1/2006 | Boas et al. |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,879 B1 | 2/2006 | Turcott |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,142,902 B2 | 11/2006 | Eda et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,216,108 B2 * | 5/2007 | Hastings ............... G06Q 30/018 |
| | | 705/63 |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,241,270 B2 | 7/2007 | Horzewski et al. |
| 7,245,953 B1 | 7/2007 | Parker |
| 7,248,910 B2 | 7/2007 | Li et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |

(56) References Cited

U.S. PATENT DOCUMENTS

| | | |
|---|---|---|
| 7,292,883 B2 | 11/2007 | De Felice et al. |
| 7,295,866 B2 | 11/2007 | Al-Ali |
| 7,319,894 B2 | 1/2008 | Higgins |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,426,407 B2 | 9/2008 | Higgins |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,483,731 B2 | 1/2009 | Hoarau et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,660,616 B1 | 2/2010 | Poore |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,725,007 B2 | 5/2010 | Moon et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,798 B2 | 12/2010 | Martinsen et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,949,380 B2 | 5/2011 | Fein et al. |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | All et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |

(56) References Cited

U.S. PATENT DOCUMENTS

| | | |
|---|---|---|
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |

(56) References Cited

U.S. PATENT DOCUMENTS

| | | |
|---|---|---|
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,058,275 B2 | 8/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |

(56) References Cited

U.S. PATENT DOCUMENTS

| | | | |
|---|---|---|---|
| 10,279,247 B2 | 5/2019 | Kiani | |
| 10,292,664 B2 | 5/2019 | Al-Ali | |
| 10,299,720 B2 | 5/2019 | Brown et al. | |
| 10,327,337 B2 | 6/2019 | Schmidt et al. | |
| 10,327,713 B2 | 6/2019 | Barker et al. | |
| 10,332,630 B2 | 6/2019 | Al-Ali | |
| 10,383,520 B2 | 8/2019 | Wojtczuk et al. | |
| 10,383,527 B2 | 8/2019 | Al-Ali | |
| 10,388,120 B2 | 8/2019 | Muhsin et al. | |
| D964,120 | 10/2019 | Forrest et al. | |
| 10,441,181 B1 | 10/2019 | Telfort et al. | |
| 10,441,196 B2 | 10/2019 | Eckerbom et al. | |
| 10,448,844 B2 | 10/2019 | Al-Ali et al. | |
| 10,448,871 B2 | 10/2019 | Al-Ali et al. | |
| 10,456,038 B2 | 10/2019 | Lamego et al. | |
| 10,463,340 B2 | 11/2019 | Telfort et al. | |
| 10,471,159 B1 | 11/2019 | Lapotko et al. | |
| 10,505,311 B2 | 12/2019 | Al-Ali et al. | |
| 10,524,738 B2 | 1/2020 | Olsen | |
| 10,532,174 B2 | 1/2020 | Al-Ali | |
| 10,537,285 B2 | 1/2020 | Shreim et al. | |
| 10,542,903 B2 | 1/2020 | Al-Ali et al. | |
| 10,555,678 B2 | 2/2020 | Dalvi et al. | |
| 10,568,553 B2 | 2/2020 | O'Neil et al. | |
| RE47,882 E | 3/2020 | Al-Ali | |
| 10,608,817 B2 | 3/2020 | Haider et al. | |
| D880,477 S | 4/2020 | Forrest et al. | |
| 10,617,302 B2 | 4/2020 | Al-Ali et al. | |
| 10,617,335 B2 | 4/2020 | Al-Ali et al. | |
| 10,637,181 B2 | 4/2020 | Al-Ali et al. | |
| D887,548 S | 6/2020 | Abdul-Hafiz et al. | |
| D887,549 S | 6/2020 | Abdul-Hafiz et al. | |
| 10,667,764 B2 | 6/2020 | Ahmed et al. | |
| D890,708 S | 7/2020 | Forrest et al. | |
| 10,721,785 B2 | 7/2020 | Al-Ali | |
| 10,736,518 B2 | 8/2020 | Al-Ali et al. | |
| 10,750,984 B2 | 8/2020 | Pauley et al. | |
| D897,098 S | 9/2020 | Al-Ali | |
| 10,779,098 B2 | 9/2020 | Iswanto et al. | |
| 10,827,961 B1 | 11/2020 | Iyengar et al. | |
| 10,828,007 B1 | 11/2020 | Telfort et al. | |
| 10,832,818 B2 | 11/2020 | Muhsin et al. | |
| 10,849,554 B2 | 12/2020 | Shreim et al. | |
| 10,856,750 B2 | 12/2020 | Indorf et al. | |
| D906,970 S | 1/2021 | Forrest et al. | |
| 10,918,281 B2 | 2/2021 | Al-Ali et al. | |
| 10,932,705 B2 | 3/2021 | Muhsin et al. | |
| 10,932,729 B2 | 3/2021 | Kiani et al. | |
| D916,135 S | 4/2021 | Indorf et al. | |
| D917,550 S | 4/2021 | Indorf et al. | |
| D917,564 S | 4/2021 | Indorf et al. | |
| D917,704 S | 4/2021 | Al-Ali et al. | |
| 10,987,066 B2 | 4/2021 | Chandran et al. | |
| 10,991,135 B2 | 4/2021 | Al-Ali et al. | |
| D919,094 S | 5/2021 | Al-Ali et al. | |
| D919,100 S | 5/2021 | Al-Ali et al. | |
| 11,006,867 B2 | 5/2021 | Al-Ali | |
| D921,202 S | 6/2021 | Al-Ali et al. | |
| 11,024,064 B2 | 6/2021 | Muhsin et al. | |
| 11,026,604 B2 | 6/2021 | Chen et al. | |
| 2001/0034477 A1 | 10/2001 | Mansfield et al. | |
| 2001/0039483 A1 | 11/2001 | Brand et al. | |
| 2002/0007198 A1 | 1/2002 | Haupert et al. | |
| 2002/0010401 A1 | 1/2002 | Bushmakin et al. | |
| 2002/0013538 A1 | 1/2002 | Teller | |
| 2002/0058864 A1 | 5/2002 | Mansfield et al. | |
| 2002/0062070 A1 | 5/2002 | Tschupp et al. | |
| 2002/0072880 A1 | 6/2002 | Svanerudh et al. | |
| 2002/0095077 A1 | 7/2002 | Swedlow et al. | |
| 2002/0133080 A1 | 9/2002 | Apruzzese et al. | |
| 2003/0013975 A1 | 1/2003 | Kiani | |
| 2003/0018243 A1 | 1/2003 | Gerhardt et al. | |
| 2003/0088165 A1 | 5/2003 | Smith et al. | |
| 2003/0106553 A1 | 6/2003 | Vanderveen | |
| 2003/0132283 A1 | 7/2003 | Hobgood et al. | |
| 2003/0144582 A1 | 7/2003 | Cohen et al. | |
| 2003/0156288 A1 | 8/2003 | Barnum et al. | |
| 2003/0212312 A1 | 11/2003 | Coffin, IV et al. | |
| 2003/0229472 A1 | 12/2003 | Kantzes et al. | |
| 2004/0034293 A1 | 2/2004 | Kimball | |
| 2004/0034294 A1 | 2/2004 | Kimball | |
| 2004/0034603 A1* | 2/2004 | Hastings | G07F 15/00 705/63 |
| 2004/0034604 A1 | 2/2004 | Hastings | |
| 2004/0106163 A1 | 6/2004 | Workman, Jr. et al. | |
| 2004/0111013 A1 | 6/2004 | Shen et al. | |
| 2004/0122300 A1 | 6/2004 | Boas | |
| 2004/0204635 A1 | 10/2004 | Scharf et al. | |
| 2004/0260154 A1 | 12/2004 | Sidelnik et al. | |
| 2004/0267103 A1 | 12/2004 | Li et al. | |
| 2005/0019936 A1 | 1/2005 | Samsoondar | |
| 2005/0055276 A1 | 3/2005 | Kiani et al. | |
| 2005/0058486 A1 | 3/2005 | Yamanaka | |
| 2005/0065417 A1 | 3/2005 | Al-Ali et al. | |
| 2005/0075548 A1* | 4/2005 | Al-Ali | A61B 5/14552 600/322 |
| 2005/0149921 A1 | 7/2005 | Rollins et al. | |
| 2005/0206518 A1 | 9/2005 | Welch et al. | |
| 2005/0221276 A1 | 10/2005 | Rozakis et al. | |
| 2005/0234317 A1 | 10/2005 | Kiani | |
| 2005/0246703 A1 | 11/2005 | Ahonen | |
| 2006/0004667 A1 | 1/2006 | Neil | |
| 2006/0025660 A1 | 2/2006 | Swedlow et al. | |
| 2006/0073719 A1 | 4/2006 | Kiani | |
| 2006/0155576 A1 | 7/2006 | Deluz | |
| 2006/0161054 A1 | 7/2006 | Reuss et al. | |
| 2006/0167351 A1 | 7/2006 | Isaacson et al. | |
| 2006/0189871 A1 | 8/2006 | Al-Ali et al. | |
| 2006/0220879 A1 | 10/2006 | Chan | |
| 2006/0220897 A1 | 10/2006 | Chan | |
| 2006/0238333 A1 | 10/2006 | Welch et al. | |
| 2007/0073116 A1 | 3/2007 | Kiani et al. | |
| 2007/0083090 A1 | 4/2007 | Sterling | |
| 2007/0093701 A1 | 4/2007 | Myers | |
| 2007/0100222 A1 | 5/2007 | Mastrototaro et al. | |
| 2007/0129622 A1 | 6/2007 | Bourget et al. | |
| 2007/0136098 A1 | 6/2007 | Smythe et al. | |
| 2007/0170073 A1 | 7/2007 | Wang et al. | |
| 2007/0180140 A1 | 8/2007 | Welch et al. | |
| 2007/0198421 A1 | 8/2007 | Muller et al. | |
| 2007/0244377 A1 | 10/2007 | Cozad et al. | |
| 2008/0033267 A1 | 2/2008 | Al-Ali et al. | |
| 2008/0064965 A1 | 3/2008 | Jay et al. | |
| 2008/0094228 A1 | 4/2008 | Welch et al. | |
| 2008/0097173 A1 | 4/2008 | Soyemi | |
| 2008/0221418 A1 | 9/2008 | Al-Ali et al. | |
| 2009/0036759 A1 | 2/2009 | Ault et al. | |
| 2009/0093687 A1 | 4/2009 | Telfort et al. | |
| 2009/0095926 A1 | 4/2009 | MacNeish, III | |
| 2009/0247924 A1 | 10/2009 | Lamego et al. | |
| 2009/0247984 A1 | 10/2009 | Lamego et al. | |
| 2009/0275813 A1 | 11/2009 | Davis | |
| 2009/0275844 A1 | 11/2009 | Al-Ali | |
| 2009/0281839 A1 | 11/2009 | Lynn et al. | |
| 2009/0299157 A1 | 12/2009 | Telfort et al. | |
| 2009/0326342 A1 | 12/2009 | Huiku | |
| 2010/0004518 A1 | 1/2010 | Vo et al. | |
| 2010/0030040 A1 | 2/2010 | Poeze et al. | |
| 2010/0069725 A1 | 3/2010 | Al-Ali | |
| 2010/0099964 A1 | 4/2010 | O'Reilly et al. | |
| 2010/0198029 A1 | 8/2010 | Wang | |
| 2010/0234718 A1 | 9/2010 | Sampath et al. | |
| 2010/0261979 A1 | 10/2010 | Kiani | |
| 2010/0270257 A1 | 10/2010 | Wachman et al. | |
| 2010/0317936 A1 | 12/2010 | Al-Ali et al. | |
| 2011/0001605 A1 | 1/2011 | Kiani et al. | |
| 2011/0028806 A1 | 2/2011 | Merritt et al. | |
| 2011/0028809 A1 | 2/2011 | Goodman | |
| 2011/0040197 A1 | 2/2011 | Welch et al. | |
| 2011/0082711 A1 | 4/2011 | Poeze et al. | |
| 2011/0087081 A1 | 4/2011 | Kiani et al. | |
| 2011/0105854 A1 | 5/2011 | Kiani et al. | |
| 2011/0118561 A1 | 5/2011 | Tari et al. | |
| 2011/0125060 A1 | 5/2011 | Telfort et al. | |

(56) References Cited

U.S. PATENT DOCUMENTS

| | | |
|---|---|---|
| 2011/0137297 A1 | 6/2011 | Kiani et al. |
| 2011/0172498 A1 | 7/2011 | Olsen et al. |
| 2011/0172967 A1 | 7/2011 | Al-Ali et al. |
| 2011/0190613 A1 | 8/2011 | Zhang |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0029301 A1 | 2/2012 | Battista |
| 2012/0059267 A1 | 3/2012 | Lamego et al. |
| 2012/0116175 A1 | 5/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0209095 A1 | 8/2012 | Huiku |
| 2012/0226117 A1 | 9/2012 | Lamego et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego et al. |
| 2013/0041591 A1 | 3/2013 | Lamego |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0157245 A1 | 6/2015 | Al-Ali et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |

(56) References Cited

U.S. PATENT DOCUMENTS

| | | |
|---|---|---|
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |

FOREIGN PATENT DOCUMENTS

| | | |
|---|---|---|
| DE | 3619442 | 12/1987 |
| DE | 3711272 | 5/1989 |
| DE | 19531520 | 1/1997 |
| EP | 0 013 278 | 7/1980 |
| EP | 0 019 278 | 11/1980 |
| EP | 0 019 478 A2 | 11/1980 |
| EP | 0 074 428 | 3/1983 |
| EP | 0 262 779 | 4/1988 |
| EP | 0 313 238 A2 | 4/1989 |
| EP | 0 329 196 | 8/1989 |
| EP | 0 104 772 B1 | 3/1990 |
| EP | 0 404 562 | 12/1990 |
| EP | 0 481 612 | 4/1992 |
| EP | 0 538 631 | 4/1993 |
| EP | 0 640 978 | 3/1995 |
| EP | 0 745 348 | 12/1996 |
| EP | 0 832 598 | 4/1998 |
| EP | 0 576 560 | 5/2000 |
| EP | 0 790 800 | 8/2000 |
| EP | 1 281 353 | 2/2003 |
| EP | 1 424 036 | 6/2004 |
| JP | 52-031736 | 3/1977 |
| JP | 62-217938 | 9/1987 |
| JP | 63-065844 | 3/1988 |
| JP | 63-050694 | 4/1988 |
| JP | 02-017462 | 1/1990 |
| JP | 02-191434 | 7/1990 |
| JP | 3135765 | 6/1991 |
| JP | 03-245042 | 10/1991 |
| JP | 04-138342 | 5/1992 |
| JP | 04-250140 | 9/1992 |
| JP | 04-306725 | 10/1992 |
| JP | 04-312447 | 11/1992 |
| JP | 05-207993 | 8/1993 |
| JP | 05-275746 | 10/1993 |
| JP | 05-334458 | 12/1993 |
| JP | 06-003890 | 1/1994 |
| JP | 06-237013 | 8/1994 |
| JP | 08-015023 | 1/1996 |

(56) References Cited

FOREIGN PATENT DOCUMENTS

| JP | 08-315919 | 11/1996 |
|---|---|---|
| JP | 09-187442 | 7/1997 |
| JP | 10-165420 | 6/1998 |
| JP | 10-314149 | 12/1998 |
| JP | 11-053662 | 2/1999 |
| JP | 11-156657 | 6/1999 |
| JP | 11-170568 | 6/1999 |
| JP | 11-185193 | 7/1999 |
| JP | 2003-506778 | 2/2003 |
| JP | 2003-521985 | 7/2003 |
| JP | 2006-512948 | 2/2006 |
| RU | 2096985 | 11/1997 |
| WO | WO 88/010462 | 12/1988 |
| WO | WO 92/001894 | 2/1992 |
| WO | WO 92/016142 | 10/1992 |
| WO | WO 96/013208 | 5/1996 |
| WO | WO 97/023159 | 7/1997 |
| WO | WO 97/029678 | 8/1997 |
| WO | WO 00/042911 | 7/2000 |
| WO | WO 01/009733 | 2/2001 |
| WO | WO 01/013790 | 3/2001 |
| WO | WO 01/030414 | 5/2001 |
| WO | WO 01/41634 | 6/2001 |
| WO | WO 01/058347 | 8/2001 |
| WO | WO 02/015781 | 2/2002 |
| WO | WO 02/017779 | 3/2002 |
| WO | WO 03/073927 | 9/2003 |
| WO | WO 04/060155 | 7/2004 |
| WO | WO 2005/011488 | 2/2005 |
| WO | WO 05/040793 | 5/2005 |
| WO | WO 06/023721 | 3/2006 |
| WO | WO 06/048840 | 5/2006 |
| WO | WO 2008/054976 | 5/2008 |

OTHER PUBLICATIONS

US 9,579,050 B2, 02/2017, Al-Ali (withdrawn)
Extended European Search Report as received in European Application No. 19205949.1, dated Apr. 29, 2020 in 5 pages.
http:--www.masimo.com-systemo.htm, "System Overview & Performance", 2 pages, reviewed on Sep. 17, 1999.
http:--www.masimo.com-pndt.htm, "Products & Technology", 1 page, reviewed on Sep. 17, 1999.
http:-www.masimo.com-cables.htm, "Patient Cables", 1 page, reviewed on Sep. 17, 1999.
http:--www.masimo.com-adt.htm, "Inop adt—Adult Disposable Digit Sensor," 1 page, reviewed on Sep. 17, 1999.
http:--www.mrequipment.com-products-oximetry_patient_mntrg.htm, "MR Equipment Magnetic Resonance Equipment Corporation, MR-Compatible High-Performance Optical Fiber Sensors, Pulse Oximetry Sensors for MRI Fiber Optic Sensors for use with MR-Compatible Pulse Oximeter", 2 pages, reviewed on Sep. 17, 1999.
Masimo Corporation, "Discrete Saturation Transforms Example", reviewed on Sep. 17, 1999.
Medical Strategic Planning, Inc., MSP Industry Alert, "Masimo to Introduce NR7 At ASA," pp. 18, 19, and the front and back cover, vol. 3, No. 3, Fall 2001.
De Kock, J.P. et al., "The Effect of Varying LED Intensity on Pulse Oximeter Accuracy", Journal of Medical Engineering & Technology, vol. 15, No. 3, May-Jun. 1991, pp. 111-116.
Reynolds, K.J., et al., "Temperature Dependence of LED and its Theoretical Effect on Pulse Oximetry", British Journal & Anaesthesia, 1991, vol. 67, pp. 638-643.
International Search Report and Written Opinion for PCT-US2007-070362, filed Jun. 4, 2007.
The International Search Report of PCT-EP2004-007042, dated Sep. 23, 2004.
Japanese Office Action dated Dec. 14, 2012 for Japanese Application No. 2009-514489.
PCT International Search Report, App. No. : PCT-US2004-023862, App. Date Jul. 26, 2004, 4 pages.
PCT International Search Report, App. No.: PCT-US2000-042637, App. Date: Jul. 12, 2000, 5 pages.
PCT International Search Report, App. No.: PCT-US2002-022712, App. Date: Jul. 17, 2002, 4 pages.
Ruckman, Jared S., "A Comparative Study of Total Hemoglobin Measurement Technology: Noninvasive Pulse Cooximetry and Conventional Methods", University of Connecticut Graduate School, Master's Theses, May 7, 2011, p. 55.
Scharf, MD, John E., "Optimization of Portable Pulse Oximetry Through Fourier Analysis", USD Department of Anesthesiology; USF Department of Electrical Engineering, 1993, pp. 233-235.
Schmitt, Joseph M., "Simple Photon Diffusion Analysis of the Effects of Multiple Scattering on Pulse Oximetry", IEEE Transactions on Biomedical Engineering, vol. 38, No. 12, Dec. 1991, pp. 1194-1203.
Wolf et al., "Correlation of Functional and Resting State Connectivity of Cerebral oxy-, deoxy-, and Total Hemoglobin Concentration Changes Measured by Near-Infrared Spectrophotometry", Journal of Biomedical Optics, Aug. 2011, vol. 16, No. 8, pp. 13.

\* cited by examiner

PARAMETER UPGRADE SYSTEM

CROSS-REFERENCE TO RELATED APPLICATIONS

The present application is a continuation of U.S. application Ser. No. 11/757,925, filed Jun. 4, 2007, entitled "Parameter Upgrade System," which claims priority benefit to U.S. Provisional Application No. 60/811,001, filed Jun. 5, 2006, entitled "Parameter Upgrade System," each of which is hereby incorporated herein by reference in its entirety.

BACKGROUND OF THE INVENTION

Physiological monitoring systems include patient monitors and corresponding noninvasive sensors for measuring constituents of circulating blood. Such patient monitoring systems have gained rapid acceptance in a wide variety of medical applications, including surgical wards, intensive care and neonatal units, general wards, home care, physical training and virtually all types of monitoring scenarios. A noninvasive sensor having light emitting diodes (LEDs) transmits optical radiation into a tissue site. A detector responds to the intensity of the optical radiation after absorption by pulsatile blood flow within the tissue site. Based upon this response, a patient monitor determines measurements for physiological parameters such as oxygen saturation, pulse rate and perfusion among others. Advanced patient monitors utilizing multiple wavelength sensors determine measurements for other physiological parameters, such as carboxyhemoglobin and methemoglobin, as examples.

SUMMARY OF THE INVENTION

A parameter upgrade system works in conjunction with a physiological monitoring system to advantageously allow a manufacturer to stock and distribute processor boards capable of measuring various combinations of physiological parameters without assigning a multitude of part numbers for each of these possible combinations. Also a parameter upgrade system easily configures processor board firmware according to the desired parameters. Firmware configuration of a processor board can be made at a place of board production, at a place of board integration into a host instrument and at end-user facilities, such as clinics or hospitals.

A parameter upgrade system advantageously uses a relatively small update tool that plugs into the sensor port of a physiological monitor so as to custom-configure the monitor's processor board with added physiological parameters. Each parameter can be added individually by a specific update tool. Additional parameters can be added in future upgrades as user requirements change. Upgrade tools can interface with various computer platforms, referred to herein generically as PCs, and be flexibly programmed, uploaded and downloaded utilizing PC-based manufacturer and field applications. Accordingly, upgrade tools have the ability to bring processor board firmware up to date and to capture and upload the history and status of multiple processor boards.

As used herein, "processor boards" refers to the hardware, including electrical and electronic components and circuits; and firmware or software, or various combinations of firmware and software, including algorithms, programs, processes, procedures and data stored in non-volatile memory or otherwise, for interfacing to a physiological monitoring system, communicating with an attached sensor or sensors and/or computing, calculating or otherwise deriving physiological parameter measurements, among other functions. Although processor board hardware and firmware are typically implemented on a printed circuit board (PCB), one of ordinary skill in the art will recognize that such functions can be implemented in various forms on various substrates including flexible circuits, hybrid circuits and ceramic substrates, to name a few.

In an embodiment, a parameter upgrade system functions in conjunction with physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, all available from Masimo Corporation ("Masimo"), Irvine, Calif. Physiological monitoring systems also include multiple wavelength sensors and corresponding noninvasive blood parameter monitors, such as Rainbow™ adhesive and reusable sensors and RAD57™ and Radical-7™ monitors for measuring $SpO_2$, pulse rate, perfusion index, signal quality, HbCO and HbMet among other parameters. The Rainbow™ sensors and RAD57™ and Radical-7™ monitors are available from Masimo Corporation, Irvine, Calif.

In other embodiments, low noise sensors are as described in at least U.S. Pat. No. 5,782,757. Patient monitors capable of reading through motion-induced noise are as described in at least U.S. Pat. Nos. 6,770,028; 6,658,276; 6,157,850; 6,002,952; 5,769,785; 5,758,644; and 5,632,272, all incorporated by reference herein. Further, noninvasive sensors include multiple wavelength optical sensors, such as described in U.S. patent application Ser. No. 11/376,013, filed Mar. 1, 2006, entitled "Multiple Wavelength Sensor Emitters;" and physiological monitors include noninvasive blood parameter monitors, such as described in U.S. patent application Ser. No. 11/367,033, filed Mar. 1, 2006, entitled "Noninvasive Multi-Parameter Patient Monitor," both patent applications assigned to Masimo Laboratories, Inc., Irvine, Calif. and both incorporated by reference herein.

DETAILED DESCRIPTION OF THE PREFERRED EMBODIMENTS

General Description

Figure 1:
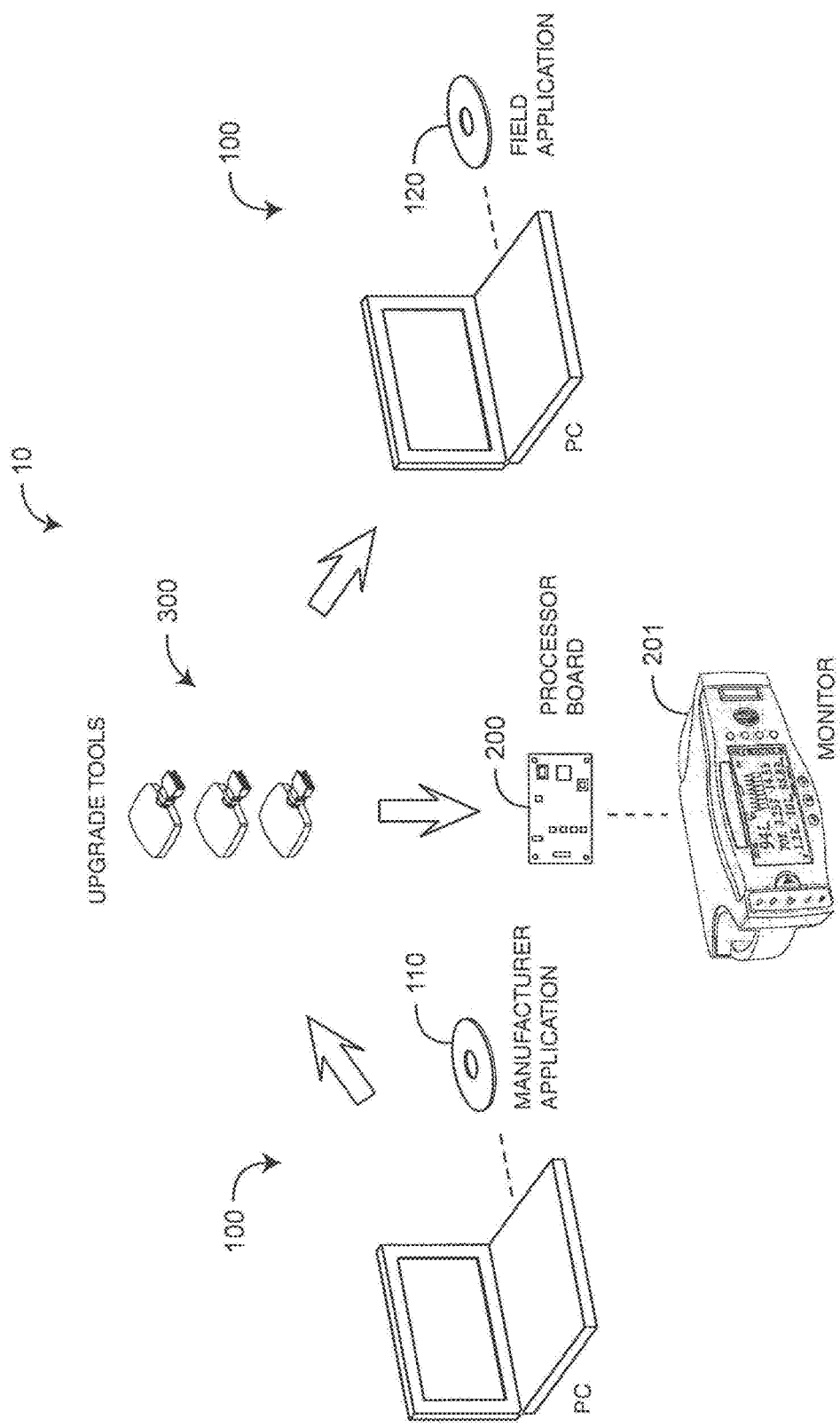
FIG. 1 is a general flow diagram of a parameter upgrade system.

FIG. 1 illustrates a parameter upgrade system 10 embodiment having application programs 100 and upgrade tools 300. The parameter upgrade system 10 as a whole controls, facilitates, tracks and documents parameter additions and firmware version upgrades for physiological monitors 201 and, in particular, for a processor board 200 located within the monitor 201. The parameter upgrade system 10 is used throughout the lifespan of the processor boards 300 to control which parameters and which revision of firmware resides on the processor boards 200. This processor board lifespan includes the time from manufacturing and functional testing to the time at a customer facility, such as an OEM manufacturer, and finally to the time "in the field" at an end-user facility, such as a hospital or medical center.

As shown in FIG. 1, upgrade tools 300 are hardware devices that provide a functional interface to processor boards 200. Upgrade tools 300 include a factory upgrade tool, a board enable tool, an end-user upgrade tool and a demo tool, as described with respect to FIG. 4, below. Each upgrade tool 300 operates independently from other tools and from the application programs 100 to perform a unique function or set of functions according to its firmware configuration. These functions include processor board firmware updates, parameter upgrades and the final enabling of processor boards. Upgrade tools 300 also retrieve logged data from the processor boards 200 they have upgraded.

Also shown in FIG. 1, a manufacturer application 110, configured to run on a PC for example, is used to initially configure the upgrade tool's functionality and assign the appropriate type and number of allowed parameter upgrades and firmware version updates. The manufacturer application 110 also reads and reports on the current status of an upgrade tool 300. Further, the manufacturer application 110 collects and documents logged data from the upgrade tool itself as well as logged data that the upgrade tool collected from processor boards 200 during upgrade sessions.

Further shown in FIG. 1, a field application 120, also configured to run on a PC, is used to read from and report on the current status of an upgrade tool 300 in the field, i.e. at an end-user facility. The field application 120 performs reading, collecting and reporting operations similar to the manufacturer application 110. The field application 120 also sends collected data and status back to the manufacturer, such as by email or other Internet connection. In an embodiment, the field application 120 is not be capable of configuring an upgrade tool 300.

Figure 2:
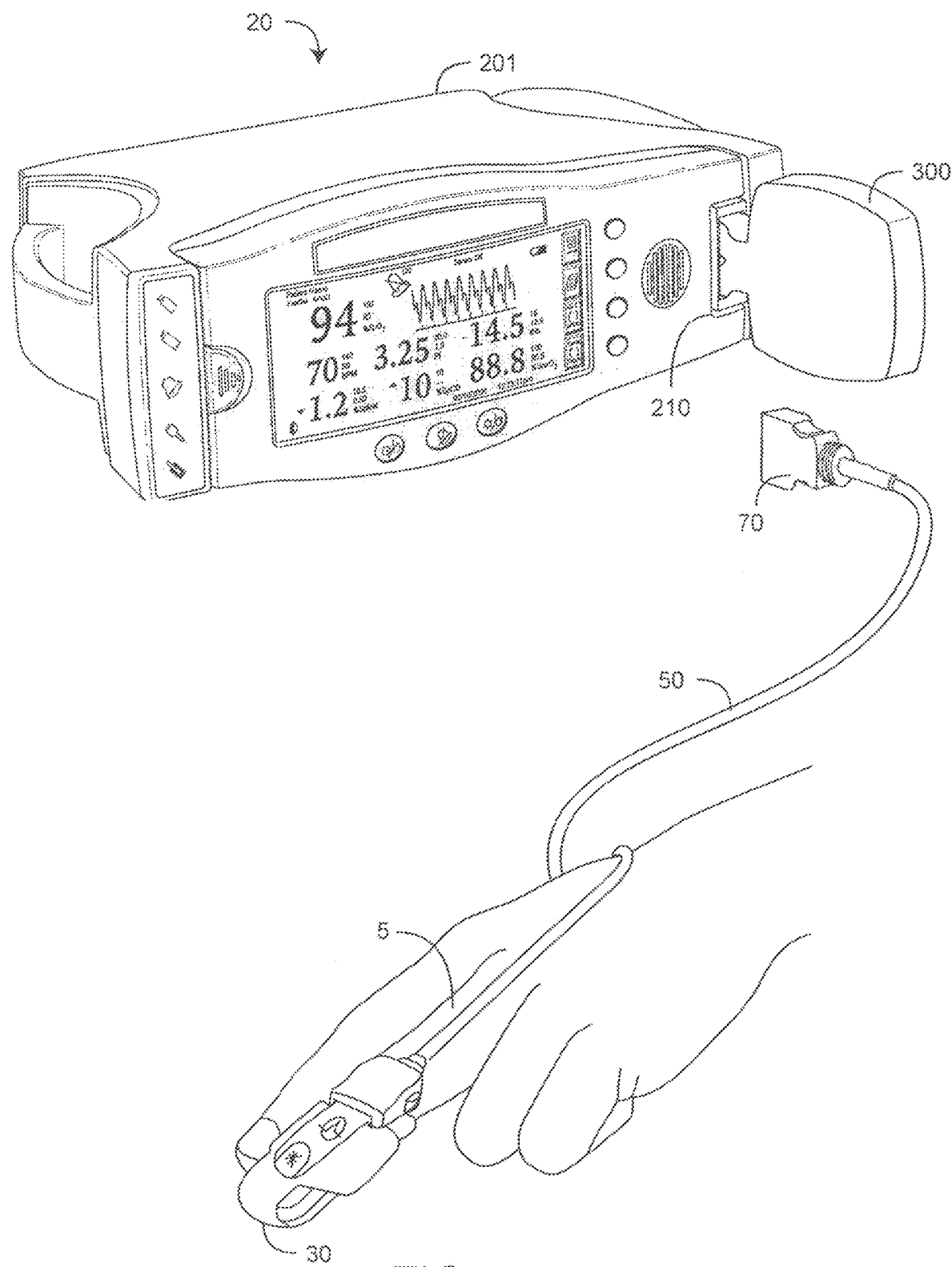
FIG. 2 is an illustration of an upgrade tool incorporated with a physiological monitoring system.

FIG. 2 illustrates a physiological monitoring system 20 including a physiological monitor 201, a sensor 30 and an interconnecting cable 50 having a monitor connector 70. The sensor 30 attaches to a patient tissue site 5, such as a fingertip. In an operational configuration (not shown), the monitor connector 70 connects to a sensor port 210 on the monitor 201. The monitor 201 operates in conjunction with the sensor 30 so as to measure and display physiological parameters of a living being, such as a patient, as described above and in further detail below. In particular, the sensor 30 is in communications with an internal processor board 200 (FIG. 3) via a sensor port 210, so that the processor board 200 (FIG. 3) can calculate physiological parameters responsive to sensor signals. In an upgrade configuration as shown, an upgrade tool 300 connects to the sensor port 210 on the monitor 201 so as to communicate with a processor board 200 (FIG. 3), upgrade processor board parameters or enable the processor board, as described in further detail below. A sensor port usable as an input/output port is disclosed in U.S. application Ser. No. 10/898,680, filed on Jul. 23, 2004, titled Multipurpose Sensor Port, which is assigned to Masimo Corporation and incorporated by reference herein.

Figure 3:
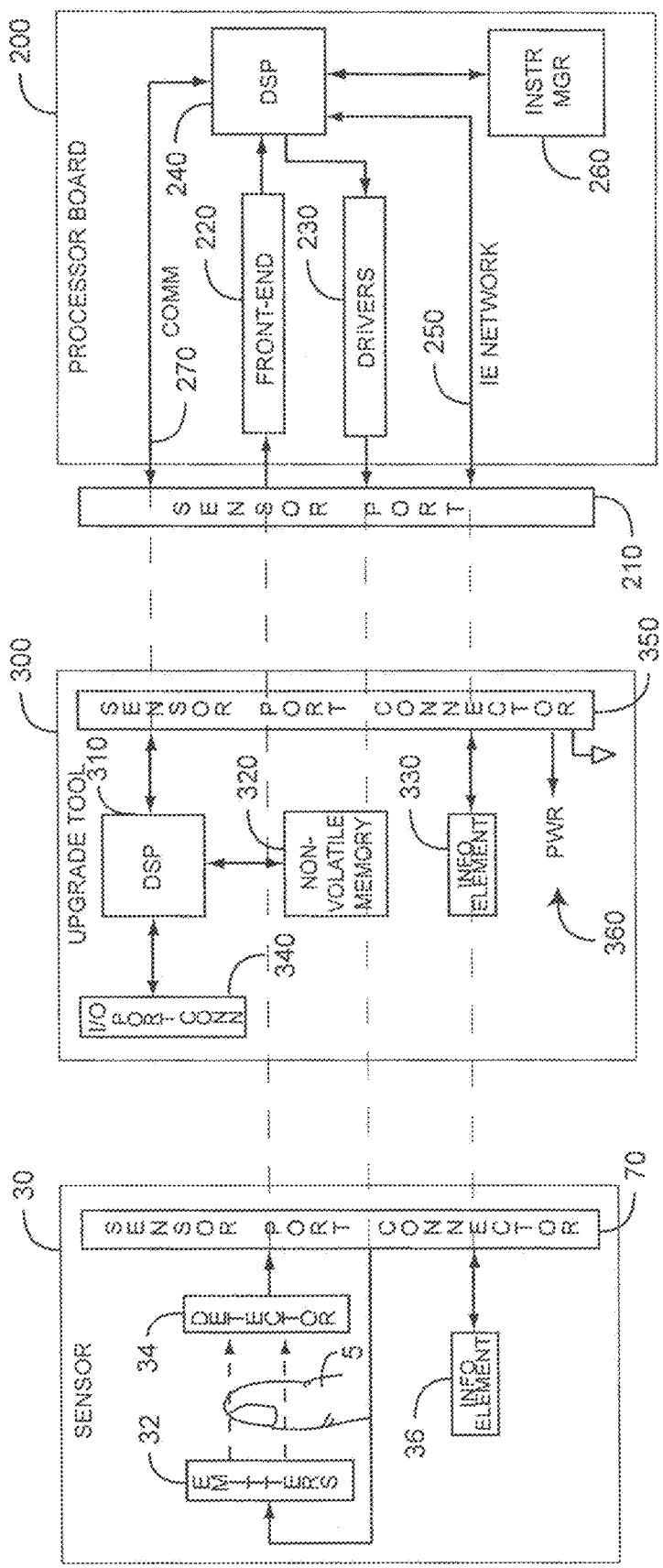
FIG. 3 is a detailed block diagram of an upgrade tool incorporated with a physiological monitoring system.

FIG. 3 illustrates a block diagram of an upgrade tool 300 incorporated with physiological monitoring system 20 (FIG. 2). The portion of the physiological monitoring system shown includes a sensor 30 and a processor board 200. In an operational mode, the sensor port connector 70 of the sensor 30 connects to a monitor sensor port 210, which is wired to the processor board 200. In this manner, the processor board 200 communicates with the sensor 30 to receive one or more intensity signal(s) indicative of one or more physiological parameters. The processor board 200 also communicates with a host instrument (not shown) via an instrument manager 260 so as to display determined parameter values calculated using the one or more intensity signals. According to an embodiment, the processor board 200 comprises processing circuitry arranged on one or more printed circuit boards capable of installation into a physiological monitor 201 (FIG. 2) or capable of being distributed as some or all of one or more OEM components for a wide variety of host instruments monitoring a wide variety of patient parameters. In an embodiment, the processor board 200 comprises drivers 230, a front-end 220, a digital signal processor ("DSP") 240 and an instrument manager 260. In general, the drivers 230 convert digital control signals into analog drive signals capable of driving sensor emitters 32. The front-end 220 converts composite analog intensity signal(s) from light sensitive detector(s) 34 into digital data input to the DSP 240. The DSP 240 has associated non-volatile memory (not shown) that stores firmware executed by the DSP, such as for deriving physiological parameter measurements.

As shown in FIG. 3, the sensor 30 includes a plurality of emitters 32 irradiating a tissue site 5 with differing wavelengths of light, and one or more detectors 34 capable of detecting the light after attenuation by the tissue 5. The processor board 200 inputs a corresponding sensor signal and is configured to determine the relative concentrations of blood constituents such as $HbO_2$, Hb, HbCO, HbMet and derive parameters such as fractional oxygen saturation, Hbt and blood glucose to name a few. For example, the sensor may be as described in U.S. application Ser. No. 11/367,013 titled Multiple Wavelength Sensor Emitters, cited above.

FIG. 3 also illustrates an upgrade tool 300, which can be programmed as a factory upgrade tool 401 (FIG. 3), a board enable tool 403 (FIG. 3), or an end-user upgrade tool 405 (FIG. 3). The upgrade tool 300 has a DSP 310, nonvolatile memory 320, an information element 330, an I/O port connector 340 and a sensor port connector 350. The DSP 310 performs the various upgrade tool functions, described with respect to FIGS. 8-10, below. The nonvolatile memory 320 stores upload and download data transmitted to and received from the I/O port 340 via an external communications path. The nonvolatile memory 320 also stores upload and download data transmitted to and received from the sensor port connector 350 via the COMM communications path 270. In an embodiment, an information element 330 may be, for example, a Dallas Semiconductor DS2506 EPROM available from Maxim Integrated Products, Inc., Sunnyvale, Calif., or equivalent. In an embodiment, IE NETWORK 250 comprises a signal conductor for transmitting and receiving serial data and a corresponding ground conductor. An information element network is described in U.S. patent application Ser. No. 11/367,036, filed Mar. 1, 2006 entitled Configurable Physiological Measurement System, which is assigned to Masimo and incorporated by reference herein. In an embodiment, the DSP is a SHARC processing device, such as available from Analog Devices. In an embodiment, COMM 270 is a bidirectional synchronous serial communications path such as implemented by one or more SPORTs (synchronous serial ports) on a SHARC DSP. In an embodiment, the I/O port connector 340 mechanically conforms with and the signals communicated thereby electrically conform with the USB (Universal Serial Bus) standard. In embodiments, the I/O port connector 340 may mechanically conform, and the signals communicated thereby electrically conform, with any of many other serial or parallel, wired or wireless interfaces, such as RS-232, IEEE-488, SCSI, IEEE 1394 (Firewire), IEEE 802.11 and expansions thereof and IEEE 802.15 (Bluetooth), to name just a few.

In an embodiment, the I/O port connector 340 mechanically conforms, and the signals communicated thereby electrically conform, with the Ethernet network standard (IEEE 802.3). Although the update tool is shown with a single I/O port connector 340, the update tool 300 may have multiple I/O ports conforming to various interface and network standards. Further, the update tool 300 may have one or more wireless transceivers in communications with the DSP 310 that conform to one or more wireless standards, such as IEEE 802.11 and expansions thereof and Bluetooth.

Further shown in FIG. 3, in addition to adding parameters to the processor board, the upgrade tool 300 can be used to update processor board firmware and download processor board data. In particular, the upgrade tool 300 communicates via a sensor port connector 350 with a physiological monitor 201 (FIG. 2) and via an I/O port connector 340 with a digital I/O device. The digital I/O device may be a PC, PDA, cellphone, pager, computer-on-wheels (COW) to name a few, or other device having a data memory and interface for communicating with the upgrade tool 300. In an embodiment, the upgrade tool 300 downloads firmware updates from a digital I/O device to nonvolatile memory 320 and uploads those updates to a physiological monitor 210 (FIG. 2). In an embodiment, the upgrade tool 300 downloads processor board data to nonvolatile memory 320 and uploads that data to a digital I/O device.

Also shown in FIG. 3, the processor board 200 reads the info element 330 to identify the upgrade tool as such. Once identified, the processor board 200 provides power 360 to the tool. The tool DSP 310 then communicates with the board DSP 240 so as to identify the type of upgrade tool, as described with respect to FIG. 4, below.

In an embodiment, processor board data includes measurement data, operational information or manufacturer information, which can be advantageously uploaded to a PC or other digital I/O device connected to the upgrade tool 300, as described above. Measurement data may comprise patient data including raw sensor data and trend data for any one or more of the measured parameters. Operational information may comprise, for example, dates and times of operation, total operating time, failure codes and event information. Failure codes indicate, for example, processor board failures and host instrument failures. Event information includes alarm data, such as a probe off occurrence and parameter measurements outside of preset limits. Manufacturer information may comprise, as examples, service information, firmware version updates and parameter upgrade dates. Service information may include firmware upgrade history and service history, including dates and times. Processor board data may also comprise processor board identification, operational information, service information and measurement data. Board identification may include serial number and current firmware version. In an embodiment, an upgrade tool may require a significant deposit so as to encourage return to the OEM for downloading the tool data and for reuse.

In various embodiments, the upgrade tool may be connected to both a digital I/O device and a physiological monitor; the upgrade tool may be connected first to one or more digital I/O devices and then to one or more physiological monitors; or the upgrade tool may be connected to one or more physiological monitors and then to one or more digital I/O devices.

Demo Tool

A demo tool (not shown) embodiment has only an information element 330 and a sensor port connector 350. The information element 330 identifies the demo tool to the processor board 200 via the IE NETWORK 250. A processor board 200 reading the information element 330 of a connected demo tool outputs simulated measurements for available parameters. This is particularly advantageous for a disabled processor board 410-420 (FIG. 4), i.e. a board unable to output measurements for available parameters until the board is enabled. In this manner, a customer or other user can verify that all desired parameters are available before creating an enabled board 430 (FIG. 4) with a board enable tool 403 (FIG. 4), which locks-out further parameter upgrades with a factory upgrade tool 401 (FIG. 4), as described below.

Upgrade Process

Figure 4:
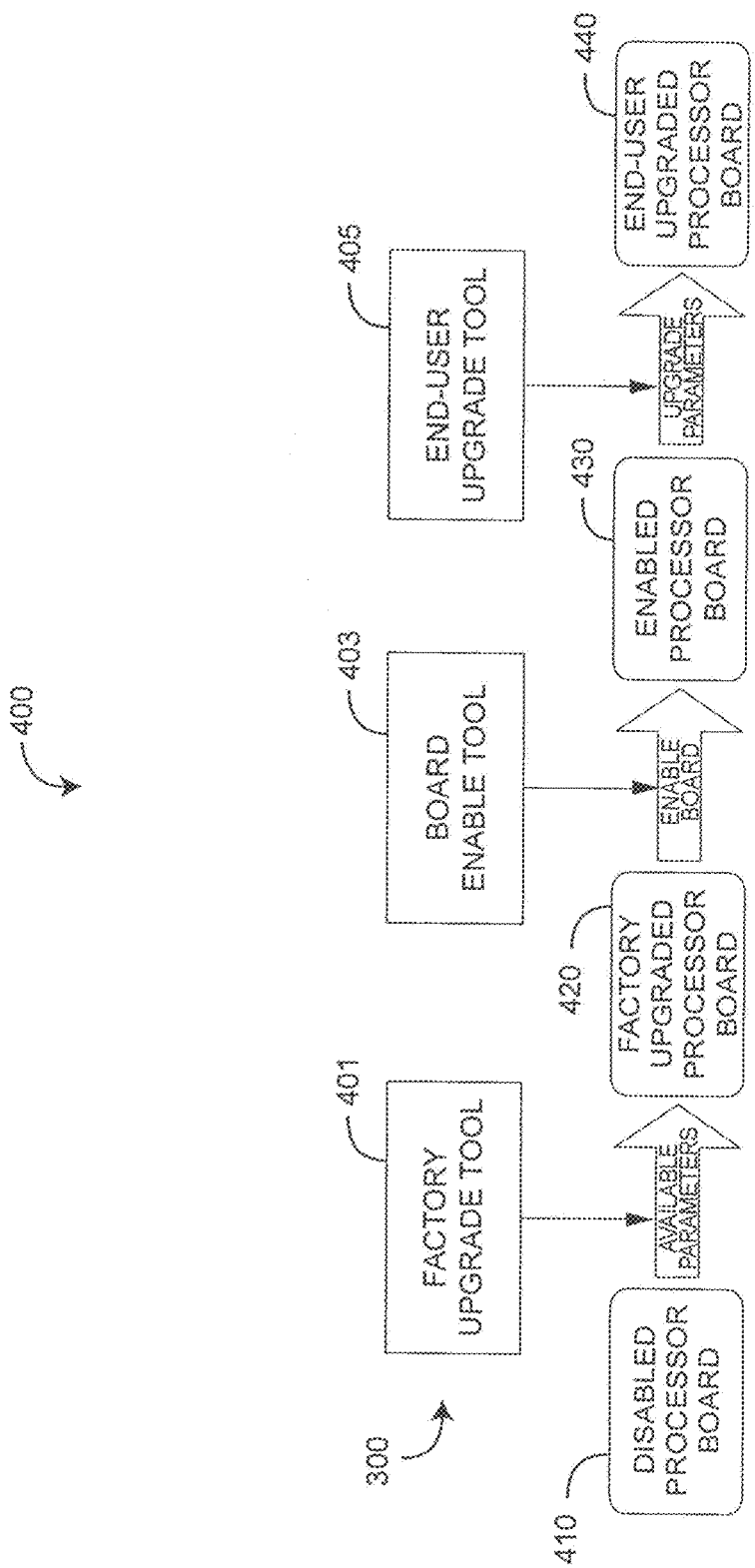
FIG. 4 is a flow diagram of a parameter upgrade process.
Figure 5B:
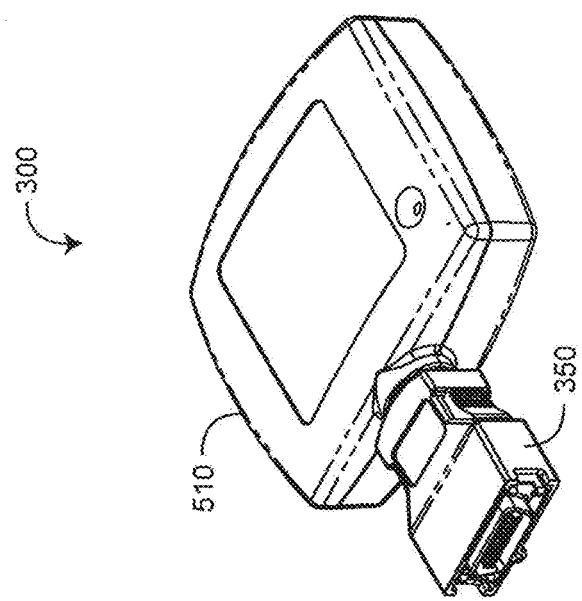
FIGS. 5A-D are top, perspective, front and side views of an upgrade tool.
Figure 5D:
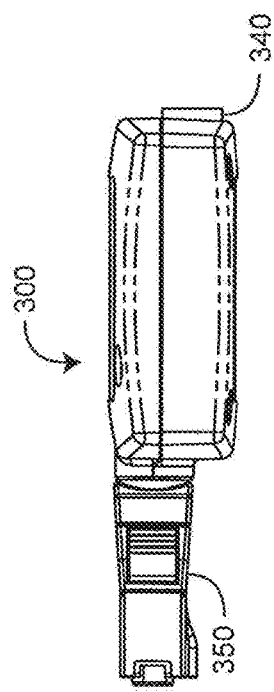
Figure 5A:
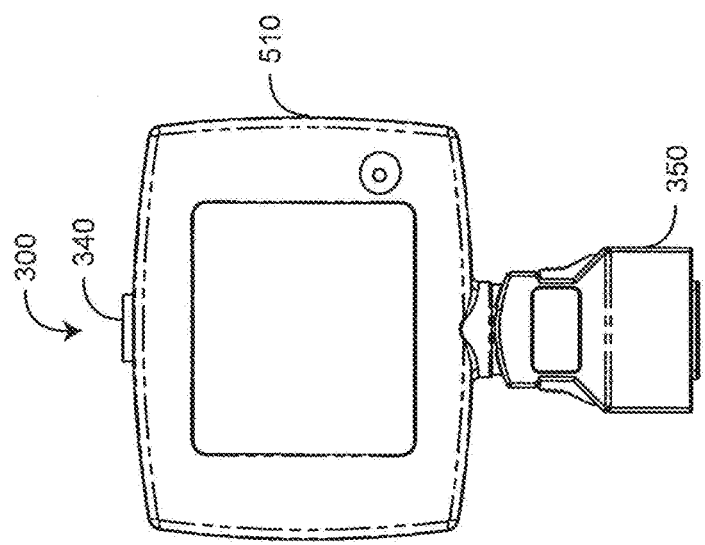
Figure 5C:
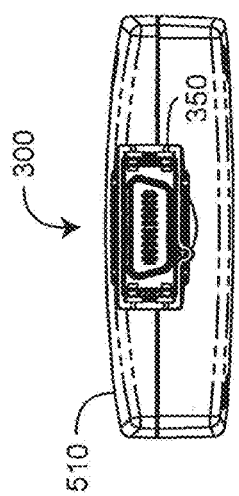

FIG. 4 illustrates a parameter upgrade process 400 where a processor board 200 (FIG. 3) undergoes multiple upgrade stages, including a disabled board 410, a factory upgraded board 420, an enabled board 430 and an end-user upgraded board 440. Multiple upgrade tools 300 are used to transition processor boards 200 (FIG. 3) between stages, including a disabled processor board 410, a factory upgraded processor board 420, an enabled processor board 430 and an end-user upgraded processor board 440, as described below. The upgrade tools 300 include a factory upgrade tool 401, a board enable tool 403 and an end-user upgrade tool 405.

In an embodiment, to facilitate the control of parameters, the processor board firmware associates a state with each parameter. Each parameter state will track whether the parameter is "available" or not. The processor board firmware will also associate a state to the entire board. This state will track whether the entire board is "enabled" or not. Disabled boards will not output measurement data for any parameter. Once enabled, boards will output measurement data for available parameters only. Additional parameters can then be upgraded to the available state. The lifespan of a processor board can be broken into four upgrade phases with regard to an example use of the parameter upgrade system, described below.

Disabled Processor Board

A disabled processor board 410 is a newly manufactured processor boards that has passed a function test and has been programmed with released firmware. The released firmware is capable of measuring all parameters but in this initial state, a disabled processor board 410 has no "available" parameters and is "disabled," which means that no parameter data is output from the board. In an embodiment, a functional test may upgrade a disabled processor board 410 to have a default set of available parameters, such as oxygen saturation, pulse rate and perfusion index. In another embodiment, a disabled processor board 410 is shipped to a customer with no parameters available, and the customer adds the default parameters along with additionally purchased parameters using one or more factory upgrade tools 401, as described below.

Factory Upgraded Processor Board

An upgrade tool that has been configured to function as a factory upgrade tool 401 can be used to upgrade the disabled processor board 410 to a factory upgraded processor board 420. This upgrade is with a single parameter, such as HbCO for example. After this upgrade, HbCO is referred to as being available. The board itself is still disabled and will not output HbCO parameter data. During this phase, multiple parameters can be upgraded to be available. In an embodiment, a different factory upgrade tool 401 must be used for each parameter. Available parameters for unenabled boards 410, 420 can be verified in a demo mode using a demo tool as described above.

Enabled Processor Board

An upgrade tool that has been configured to function as a board enable tool 403 is used to "enable" the factory upgraded processor board 420 to an enabled processor board 430. An enabled board 330 is capable of sending parameters to a host instrument. After the board is enabled, any available parameters will be measured and output with the appropriate sensors. Once a board is enabled, it can no longer be upgraded with a factory upgrade tool 401. From this point on, only an end-user upgrade tool 405 can be used to upgrade the board with additional parameters or firmware updates.

End-User Upgraded Board

This phase represents the rest of a processor board's lifespan. Additional parameters can be added to an enabled processor board 430 with an end-user upgrade tool 405 only and is designated an end-user upgraded processor board 440. In an embodiment, as with the factory upgrade tool 401, a different end-user upgrade tool 405 must be used for each parameter to be added. All available parameters will remain available for the remaining lifespan of the board. In an embodiment, an upgrade tool 400 also can be used during the upgrade processes described above to advantageously update processor board firmware to the latest version and to retrieve various processor board data from one or more processor boards, as described in detail below. The above describes but one example use of the parameter upgrade system.

Upgrade Tool Configuration

Figure 6:
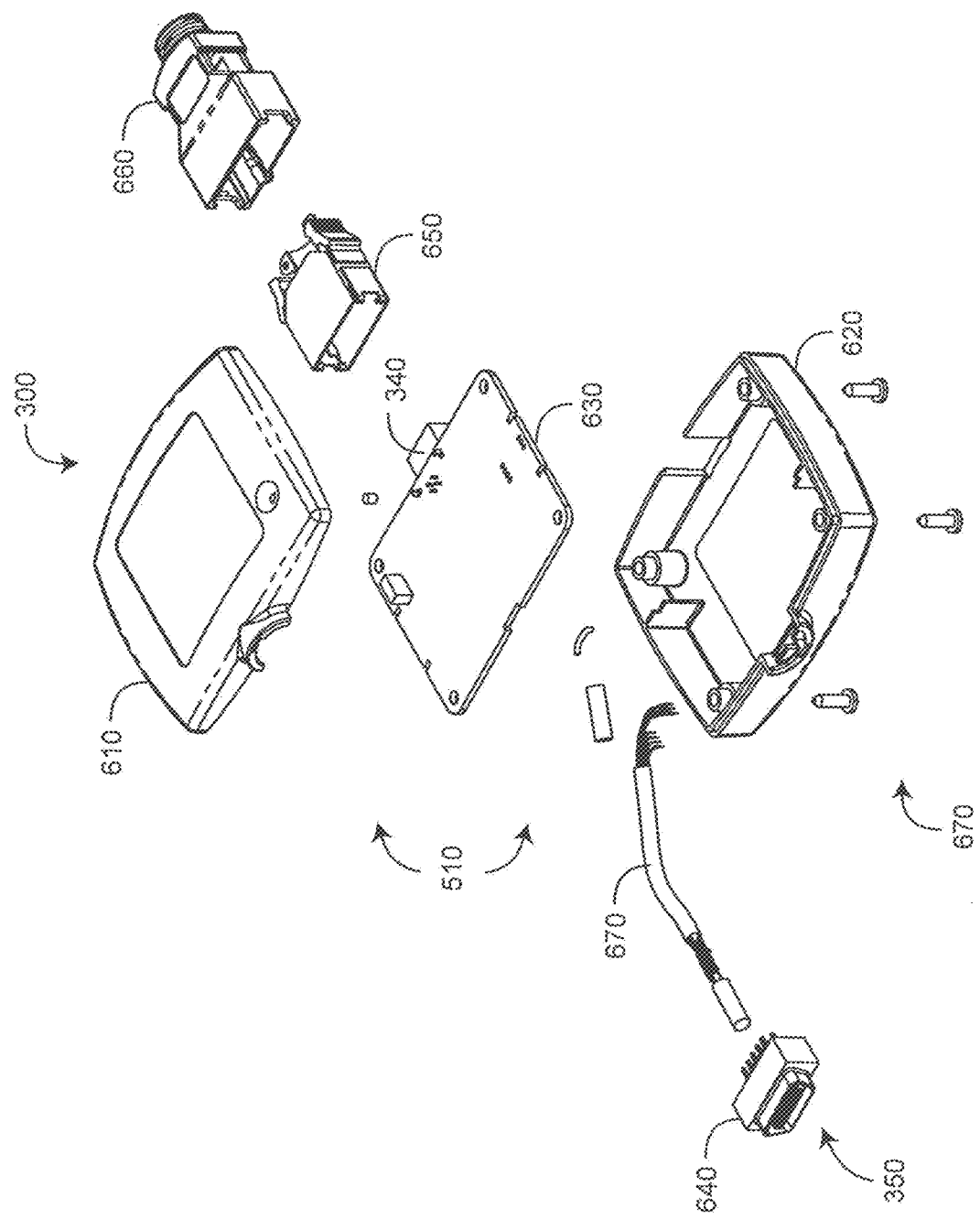
FIG. 6 is an exploded view of an upgrade tool.

FIGS. 5-7 illustrate an upgrade tool 300 embodiment. As shown in FIGS. 5A-D, an upgrade tool 300 has a case 510, an I/O port connector 340 and a sensor port connector 350, as described above. In the embodiment shown, the I/O port connector 340 is a USB connector, and the sensor port connector 350 is a 20-pin connector.

As shown in FIG. 6, the case 510 has an upper cover 610 and a lower cover 620, which are attached together with fasteners 670 to enclose a circuit board 630. The circuit board 630 mechanically mounts and electrically connects the DSP 310 (FIG. 3), non-volatile memory 320 (FIG. 3) and info element 330 (FIG. 3) and associated "glue" circuits, conductors and components. The sensor port connector 350 has a connector block 640, a clip 650, a shell 660 and a cable 670. The cable 670 interconnects the connector block 640 and the circuit board 630. The connector block 640 provides pins for electrically attaching wires from one end of the cable 670 and connector contacts for mating with corresponding sensor port 210 (FIG. 1) contacts. The clip 650 provides a finger releasable hold to the sensor port 210 (FIG. 1) connector. The shell 660 houses the connector block 640 and clip 650 and provides a strain relief mount to the case 510.

Figure 7C:
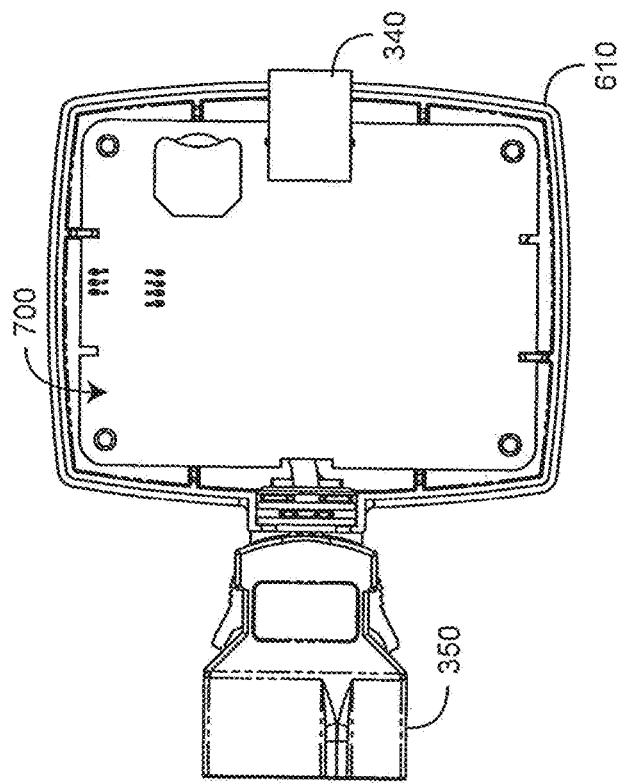
FIGS. 7A-C are perspective, front and bottom partial assembly views of an upgrade tool.
Figure 7A:
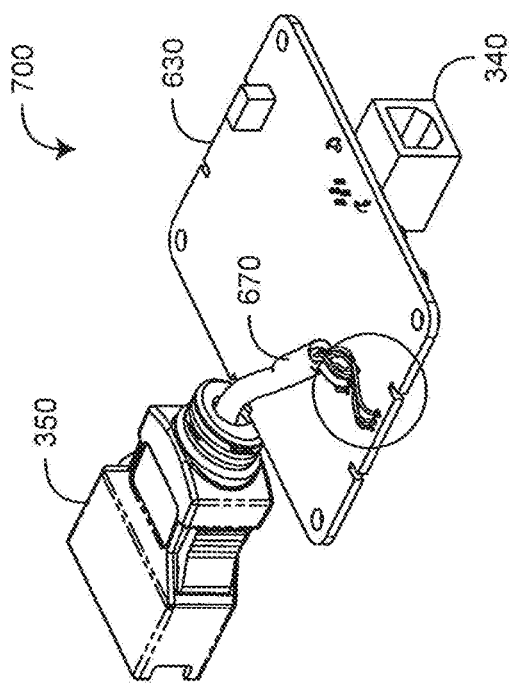
Figure 7B:
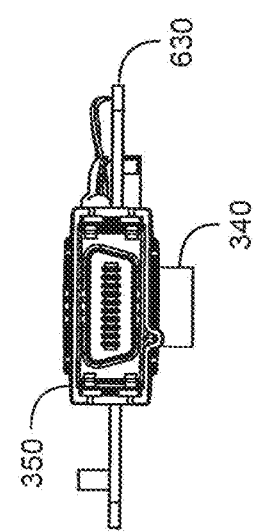

As shown in FIGS. 7A-C, a circuit board assembly 700 has the sensor port connector 350 mounted to the circuit board 630 via the cable 670. The circuit board assembly 700 mounts into the upper cover 610 so that the circuit board 630 is enclosed within the case 510 (FIG. 6) and secured by the fasteners 670 (FIG. 6) and so that the I/O port connector 340 and sensor port connector 350 are exposed.

Upgrade Tool Functions

Figure 8A:
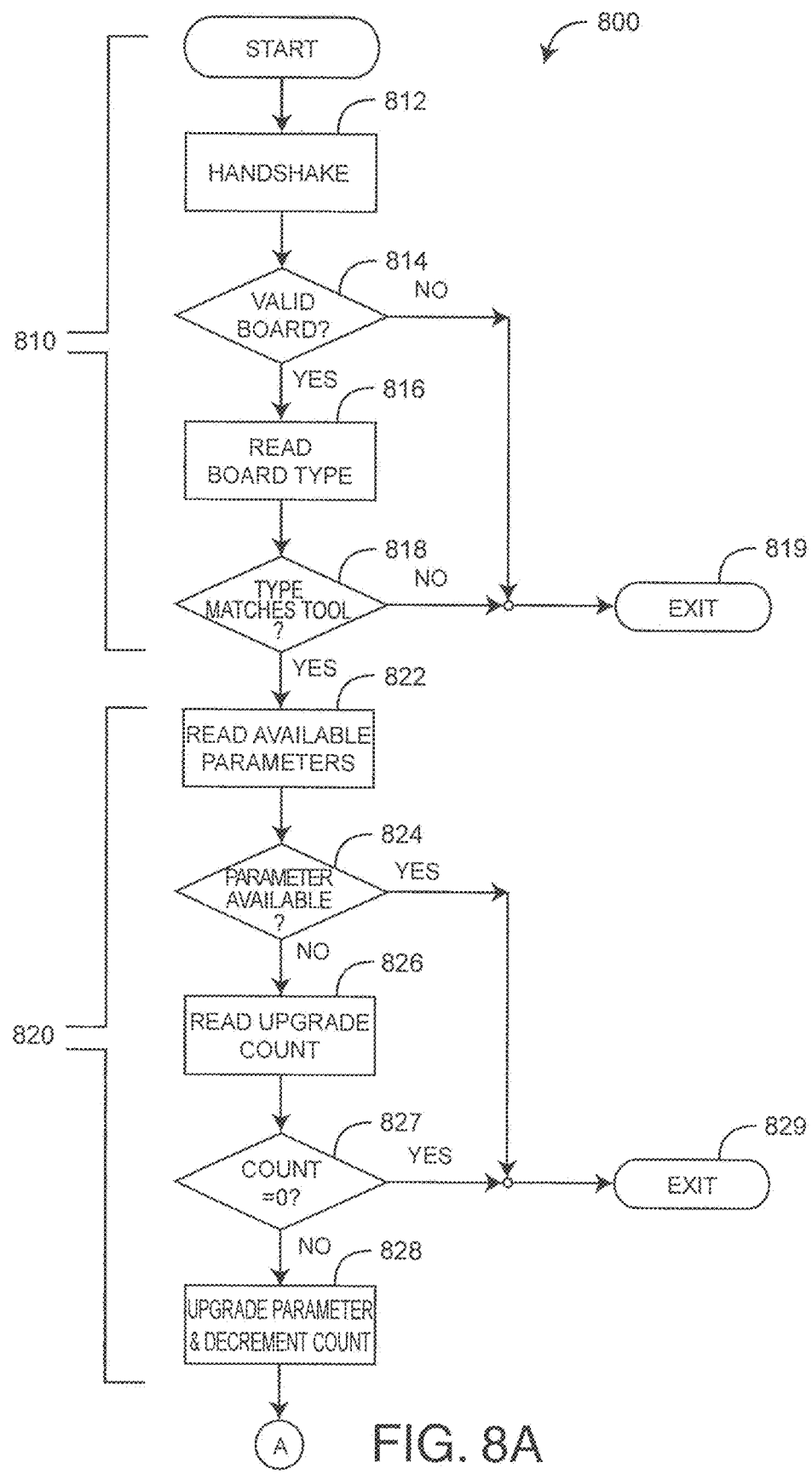
FIGS. 8A-B is a flowchart of upgrade tool operational functions.
Figure 8B:
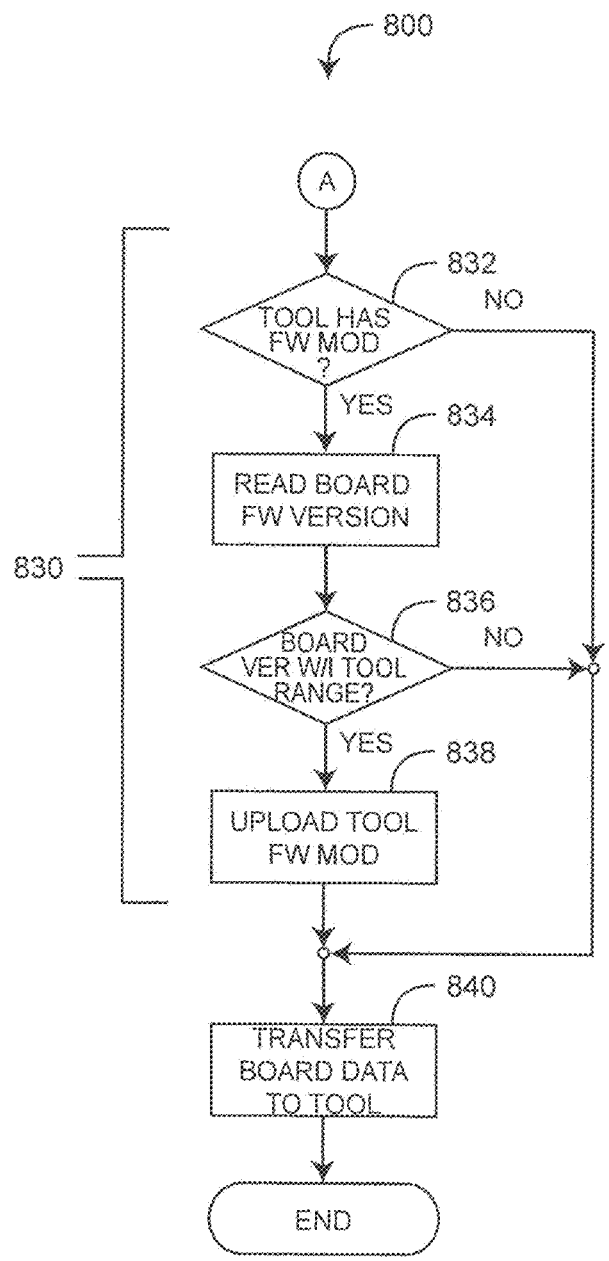
Figure 9:
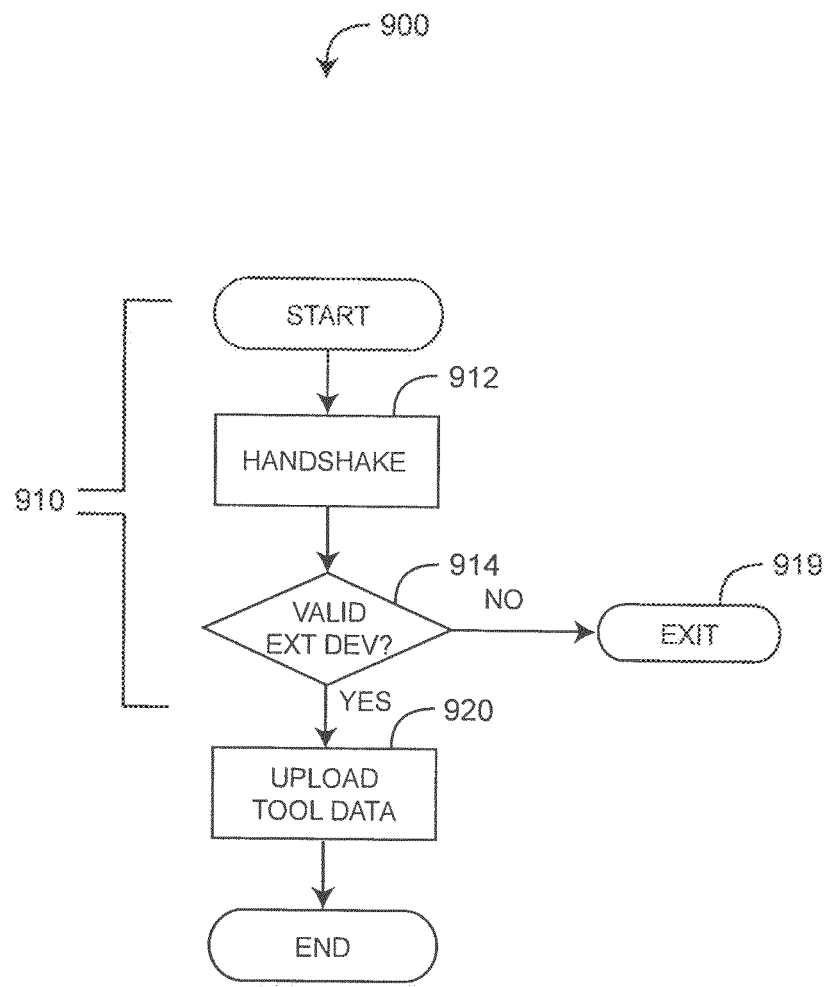
FIG. 9 is a flowchart of upgrade tool read functions.
Figure 10:
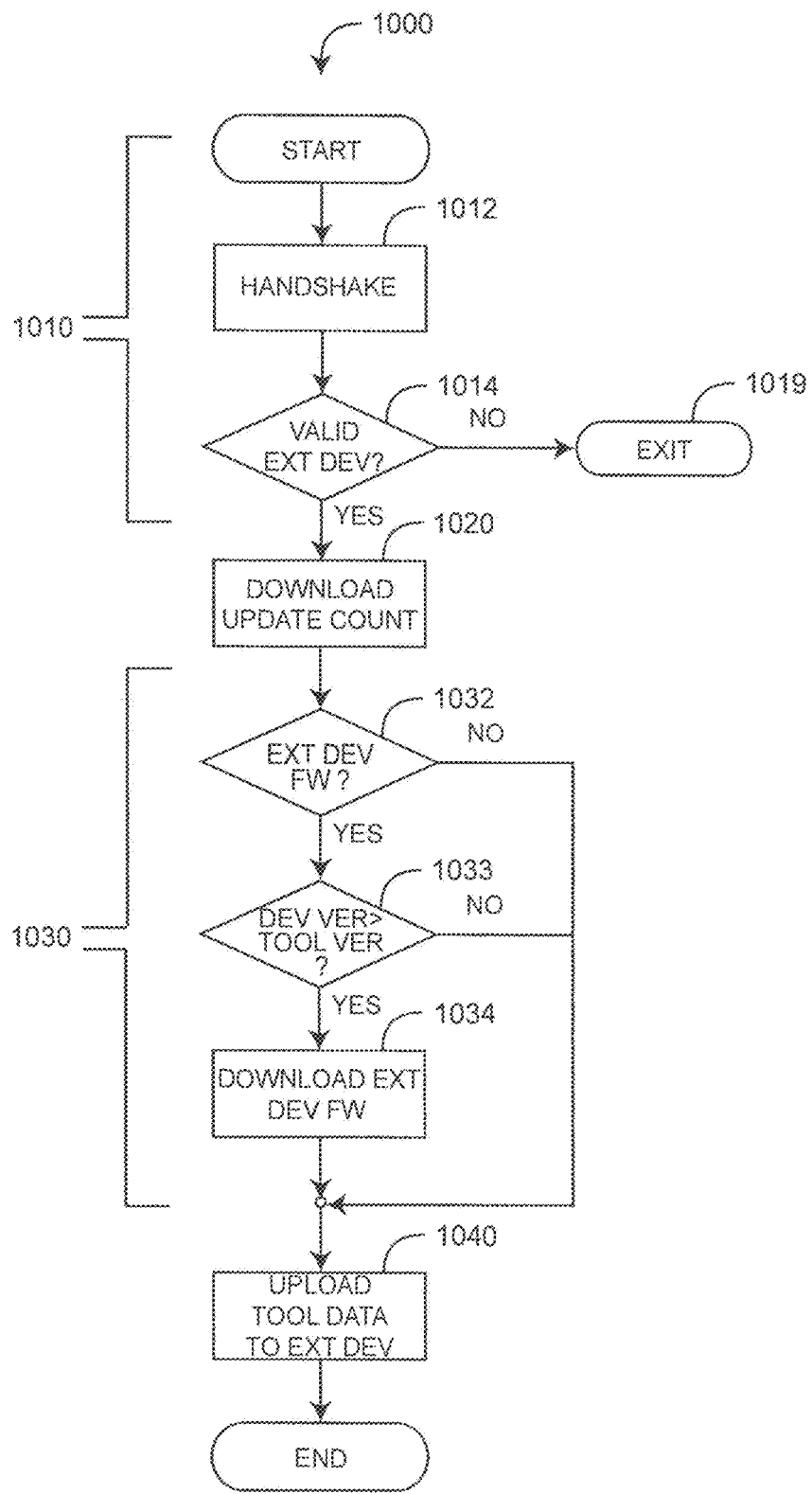
FIG. 10 is a flowchart of upgrade tool maintenance functions.

FIGS. 8-10 illustrate upgrade tool functions, which include processor board functions 800 (FIGS. 8A-B), tool reading functions 900 (FIG. 9) and tool maintenance functions 1000 (FIG. 10). Corresponding graphical user interfaces (GUIs) are described with respect to FIGS. 11 and 12, below. As shown in FIGS. 8A-B, processor board functions 800 involve upgrade tool 300 (FIG. 3) communications with a processor board 200 (FIG. 3) via the COMM path 270 (FIG. 3) and the sensor port 210 (FIG. 3). Processor board functions 800 include processor board authentication 810, parameter upgrade administration 820, uploading processor board firmware modifications 830 and downloading processor board data 840. Processor board authentication 810 includes verification that a valid processor board is connected to the sensor port. This verification includes transmission and receipt of an encrypted handshake 812 between the upgrade tool and the processor board. This handshake is successful only if the upgrade tool recognizes the processor board 814 and the processor board recognizes the tool. Processor board authentication 810 also includes board type determination 816 and matching 818 the upgrade tool type, i.e. factory tool or end-user tool to the processor board type, i.e. a disabled board 410, 420 (FIG. 4) or an enabled board 430, 440 (FIG. 4). If the processor board does not authenticate or there is a mismatch between tool type and board type, e.g. a factory tool is connected to an enabled board, then the upgrade tool performs no action 819 with respect to the connected processor board.

As shown in FIGS. 8A-B, parameter upgrade administration 820 includes reading the available parameters 822 from the processor board and verifying the tool upgrade count 826. If and only if the tool specific parameter is currently unavailable on the processor board 824 and the tool upgrade count is not zero 827, is the processor board parameter made available. Otherwise, the upgrade tool performs no action 829. The upgrade count is decremented accordingly 828.

Further shown in FIGS. 8A-B, uploading processor board firmware modification 830 includes determining if the tool contains a firmware modification 832, reading the board firmware version number 834 and replacing the processor board firmware with the tool firmware modification 838 if and only if the processor board version number is within the range defined in the tool 836. The downloading processor board data 840 includes transferring the processor board data into the tool and storing the data in tool nonvolatile memory according to a processor board identifier.

FIG. 9 illustrates the tool reading functions 900, which involve communications with an external digital device, such as a PC, via the I/O port 340 (FIG. 3). External device authentication 910 verifies that an authorized external device is accessing an upgrade tool. This verification includes receipt and transmission of an encrypted handshake between the upgrade tool and the external device 912. This handshake is successful only if the upgrade tool recognizes the external device 914. Otherwise, the tool is non-responsive 919 to the attached device. The upload tool data 920 transfers tool specific data to the external device, such as described with respect to FIG. 10, below.

FIG. 10 illustrates the tool maintenance functions 1000, which also involve communications with an external digital device, such as a PC, via the I/O port 340 (FIG. 3). Tool maintenance functions 1000 include external device authentication 1010, downloading parameter upgrades 1020 and firmware modifications 1030 from the external digital device and uploading processor board history 1040 to the external digital device. External device authentication 1010 verifies that an authorized external device is accessing an upgrade tool. This verification includes receipt and transmission of an encrypted handshake between the upgrade tool and the external device 1012. This handshake is successful only if the upgrade tool recognizes the external device 1014. Otherwise, the tool is non-responsive 1019 to the attached device. The parameter upgrade download 1020 indicates the tool parameter and the number of authorized parameter upgrades for that parameter. Further, if the external device has a processor board firmware update 1032, that firmware is downloaded into the tool 1034. Also, any processor board data previously downloaded into the tool from one or more processor boards is uploaded into the external device 1040.

PC Interface

Figure 11:
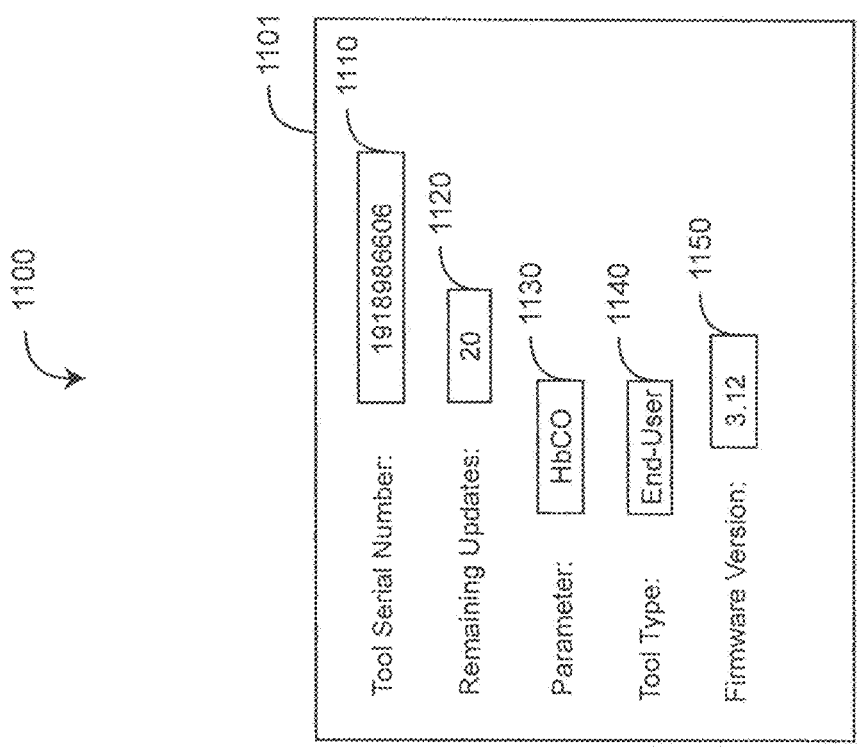
FIG. 11 is an illustration of a field application graphical user interface (GUI)
Figure 12:
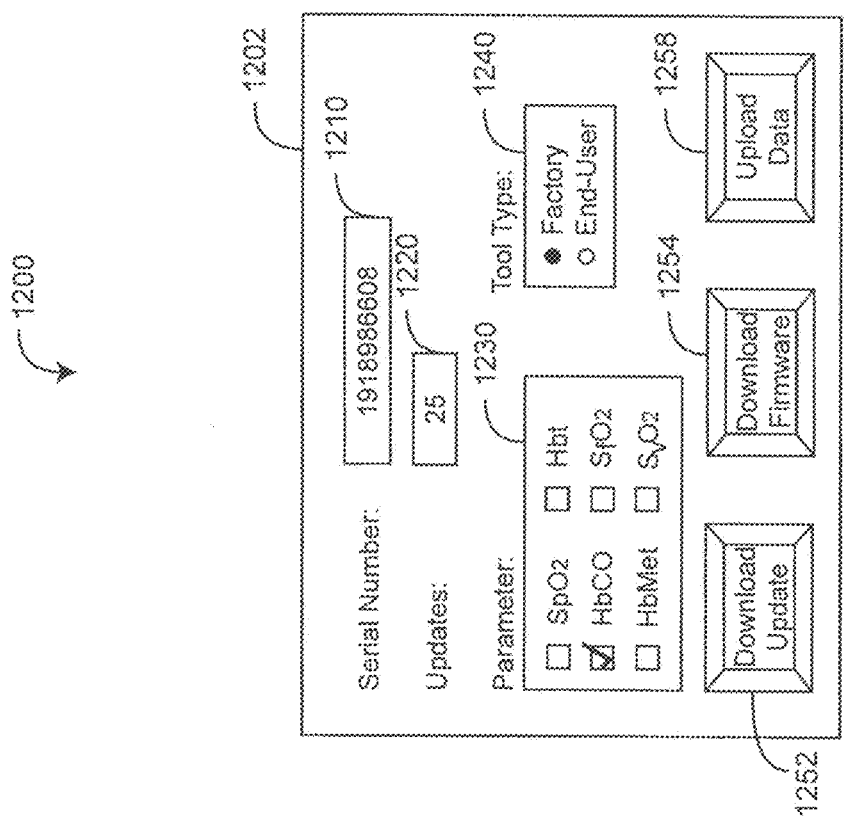
FIG. 12 is an illustration of a manufacturer application GUI.

FIGS. 11-12 illustrate a graphical user interfaces (GUIs) for a field application 120 (FIG. 1) and a manufacturer application 110 (FIG. 1), respectively. As shown in FIG. 11, in a field application GUI 1100 embodiment, a PC provides an interface for a customer or end-user to "read" a factory upgrade tool 401 (FIG. 4) or an end-user tool 405 (FIG. 4). In particular, a user can determine a tool serial number 1110, the remaining number of upgrades 1120, the tool parameter 1130, the tool type 1140 and the firmware version 1150. The process is read only, i.e. the user cannot alter the tool or read other data stored in the tool.

As shown in FIG. 12, in a manufacturer GUI 1202 embodiment, a PC provides an interface for a manufacturer to both read and modify a tool. The tool serial number 1210 can be displayed. The number of upgrades 1220, the tool parameter 1230 and the tool type 1240 can also be displayed and modified.

Networking and Wireless Applications

Figure 13:
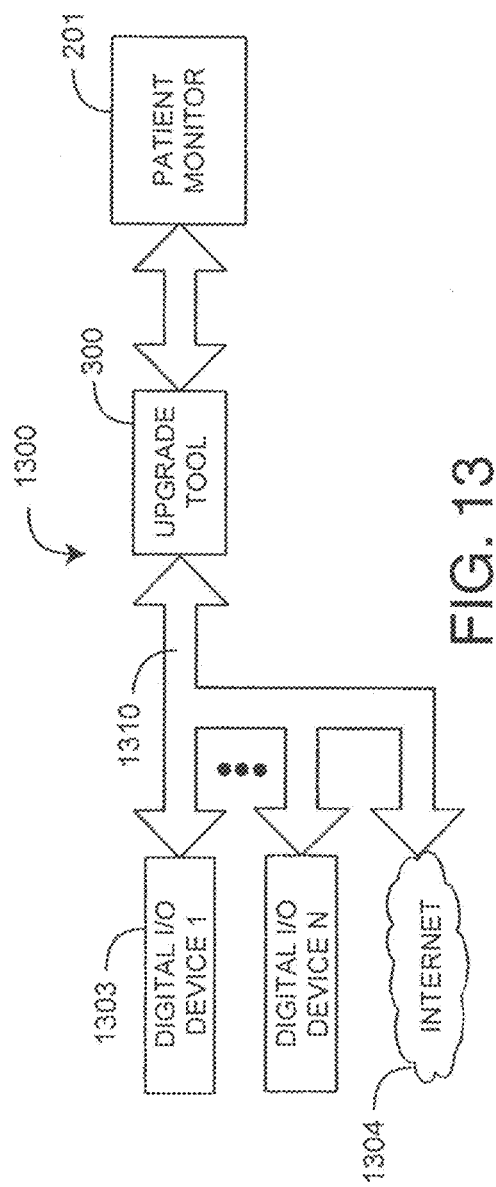
FIG. 13 is a block diagram of a network configuration for an upgrade tool.

FIG. 13 illustrates an upgrade tool networking application 1300. An upgrade tool 300 interconnects a physiological monitor 201 via a sensor port 210 (FIG. 3) with a network 1310 via an I/O port 340 (FIG. 3), such as an Ethernet compatible interface. In this manner, the upgrade tool 300 can communicate with one or more digital I/O devices 1303, as described above, or gain access to the Internet 1304. In an embodiment, when the upgrade tool 300 is connected to the physiological monitor 201, the upgrade tool accesses a central website via the network 1310 (or a wireless connection as described below) and the Internet 1304 so as to download the latest firmware updates, which are made accessible from the website. These firmware updates are then uploaded to a corresponding processor board within the physiological monitor 201, as described above.

Figure 14:
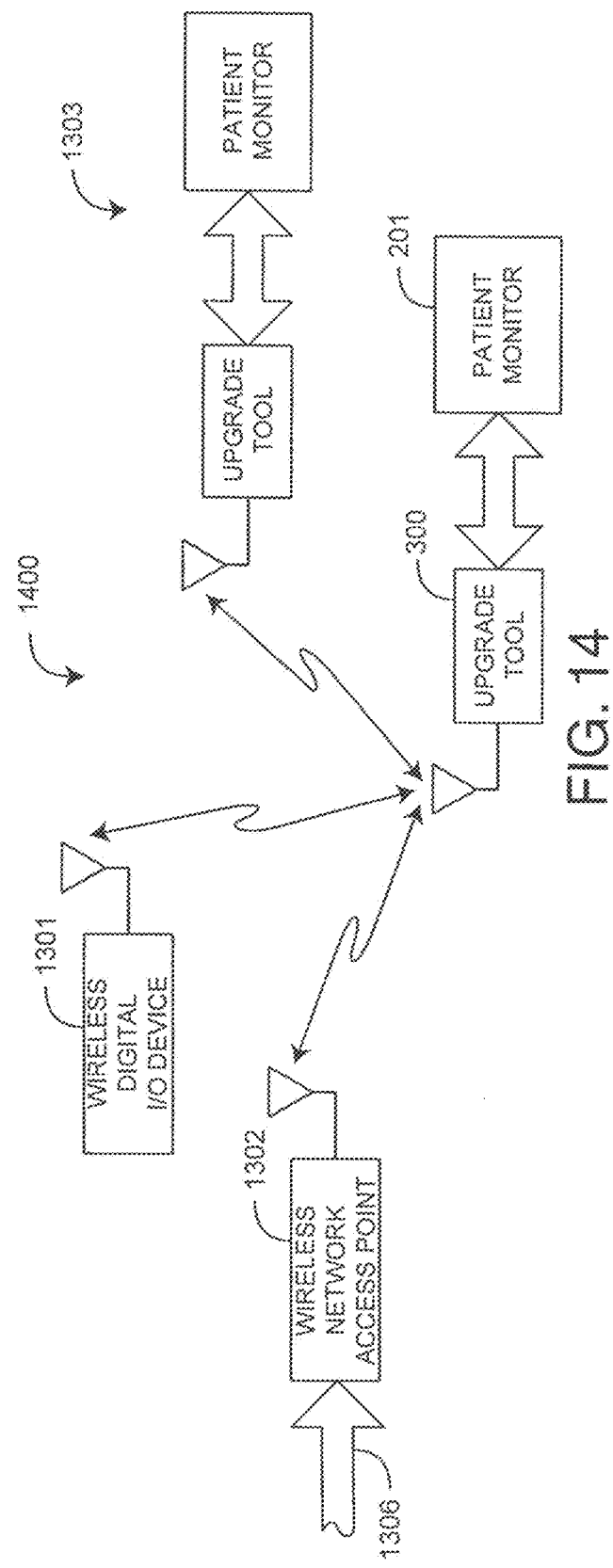
FIG. 14 is a block diagram of a wireless configuration for upgrade tools.

FIG. 14 illustrates an upgrade tool networking application 1400. In an embodiment, an upgrade tool 300 interconnects a physiological monitor 201 via a sensor port 210 (FIG. 3) with a wireless transceiver via an I/O port 340 (FIG. 3). The wireless transceiver is compliant with a wireless standard, such as IEEE-802.11 or IEEE 802.15 (Bluetooth). In an embodiment, the upgrade tool 300 provides wireless communications with a wireless digital I/O device 1301. In an embodiment, the upgrade tool 300 provides wireless communications with a wireless network access point 1302. In an embodiment, the upgrade tool 300 also has a network I/O port in communications with a network, such as described with respect to FIG. 13, above, and acts as a network access point for a second wireless upgrade tool connected to a second physiological monitor 1303. In other embodiments, an upgrade tool connected to any power source and a wired or wireless downloads firmware updates or any other data and uploads stored data while in communication with a manufacturer server or other secure computer.

Tiered Parameter Pricing

Figure 15:
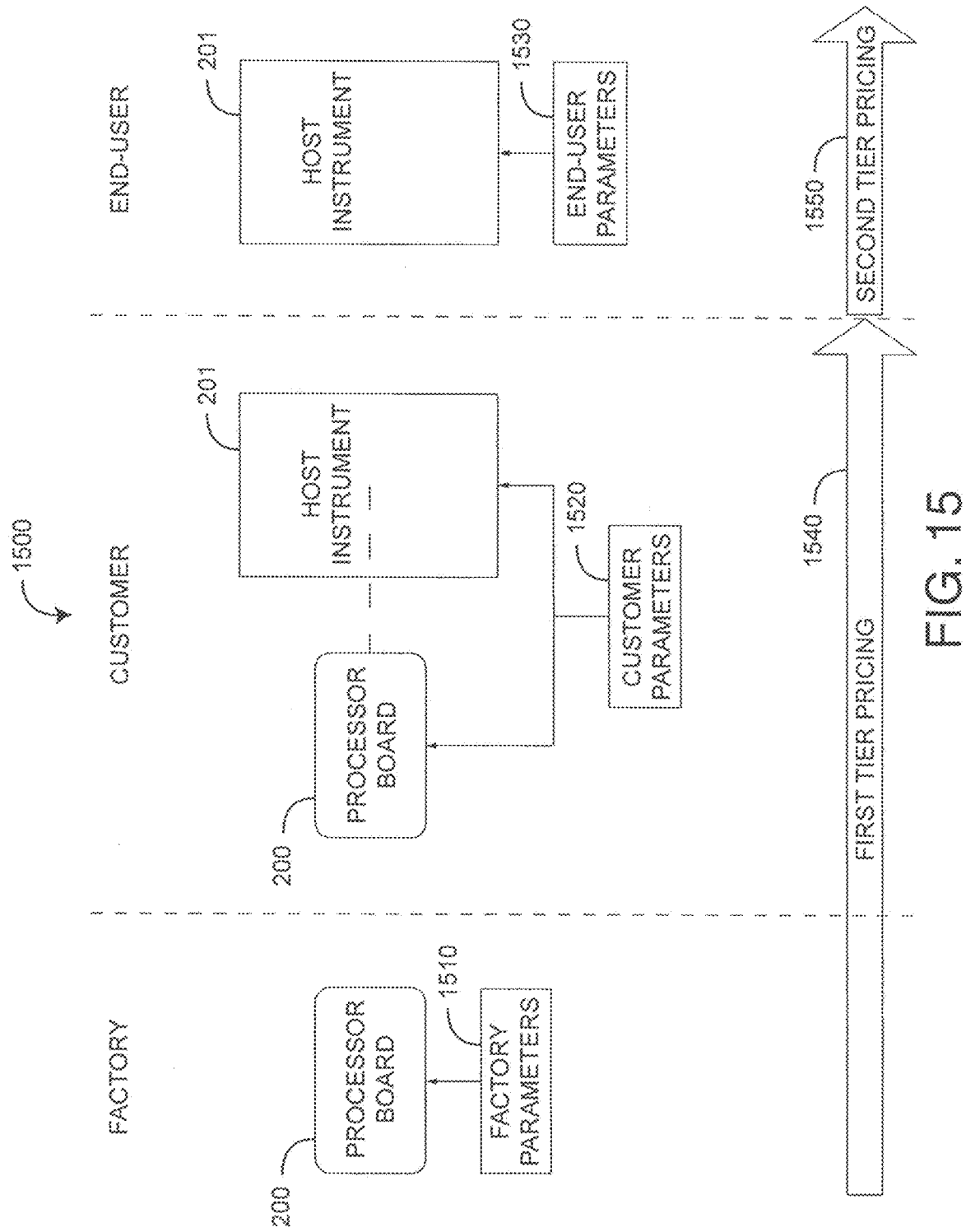
FIG. 15 is a block diagram of a two-tier parameter pricing structure.

FIG. 15 illustrates two-tiered parameter pricing for a processor board 200, such as described with respect to FIG. 3, above. As described above, the processor board 200 has the capability to measure multiple physiological parameters. As described above, a parameter upgrade process 400 (FIG. 4) provides a flexible pricing plan for these multiple parameters. In an embodiment, parameters can be made available individually to individual boards, providing processor boards that are custom-configurable to fit customer needs.

In an embodiment, parameter programming can occur at a factory, a customer or an end-user facility. Factory parameters 1510 include default parameters added to a newly manufactured processor board 200. Customer parameters 1520 include additional parameters added to a processor board 200 in conjunction with the incorporation of the processor board within a host instrument 201, as described with respect to FIGS. 3-4, above. End-user parameters 1530 include additional parameters that are made available to an enabled processor board 200 integrated into an operational host instrument 201 sold or otherwise provided to an end-user, such as a hospital or medical facility.

In an advantageous embodiment, a parameter upgrade system is configured so as to provide a self-enforcing, two-tier parameter pricing structure. A first tier pricing 1540 applies to factory parameters 1510 and customer parameters 1520. A second tier pricing 1550 applies to end-user parameters 1530. As one example, first tier pricing 1540 applies a lower price for one or more of the available parameters as compared to the second tier pricing 1550.

A parameter upgrade system has been disclosed in detail in connection with various embodiments. These embodiments are disclosed by way of examples only and are not to limit the scope of the claims that follow. One of ordinary skill in art will appreciate many variations and modifications. For example, in an embodiment, upgrade tools 300 (FIG. 3) spread firmware updates between processor boards in a viral manner, i.e. downloading a detected higher version firmware from a processor board and uploading the firmware to other processor boards that have lower version firmware.

What is claimed is:

1. A physiological monitor comprising:
  a sensor port configured for attachment and communication with a sensor and further configured for attachment and communication with a handheld upgrade tool in lieu of the sensor;
  one or more processors in communication with the sensor port; and
  a data store storing a plurality of firmware instructions, the plurality of firmware instructions comprising:
    a first set of firmware instructions relating to calculation of at least one first physiological parameter in response to a sensor signal received from the sensor, wherein the first set of firmware instructions is made available to the one or more processors, and
    a second set of firmware instructions relating to calculation of at least one second physiological parameter in response to the sensor signal received from the sensor, wherein the second set of firmware instructions is not made available to the one or more processors, wherein the one or more processors are configured to:
   determine that the handheld upgrade tool is attached to the sensor port,
   determine whether the handheld upgrade tool is authorized to access the physiological monitor,
   determine whether a tool type of the handheld upgrade tool corresponds to a processor board type associated with the physiological monitor, and
   based at least in part on a determination that the tool type corresponds to the processor board type, a determination that the handheld upgrade tool is authorized to access the physiological monitor and a determination that the physiological monitor is authorized to access the handheld upgrade tool, receive an update to the plurality of firmware instructions from the handheld upgrade tool, wherein the update to the plurality of firmware instructions makes available to the one or more processors the second set of firmware instructions.

2. The physiological monitor of claim 1, wherein the handheld upgrade tool determines whether the physiological monitor is authorized to access the handheld upgrade tool.

3. The physiological monitor of claim 1, wherein the one or more processors are further configured to, based at least in part on a determination that the tool type does not correspond to the processor board type, determine that the handheld upgrade tool is not authorized to access the physiological monitor.

4. A method for updating firmware instructions on a physiological monitor comprising:
   determining, using one or more processors of the physiological monitor, that a handheld upgrade tool is attached to a sensor port of the physiological monitor in lieu of a sensor;
   determining, using the one or more processors of the physiological monitor, that the handheld upgrade tool is authorized to access the physiological monitor; and
   based at least in part on said determining that the handheld upgrade tool is authorized to access the physiological monitor, and a determination that the physiological monitor is authorized to access the handheld upgrade tool, receiving from the handheld upgrade tool an update to a plurality of firmware instructions stored in a data store of the physiological monitor,
   wherein the plurality of firmware instructions comprises a first set of firmware instructions relating to calculation of at least one first physiological parameter in response to a sensor signal received from the sensor and a second set of firmware instructions relating to calculation of at least one second physiological parameter in response to the sensor signal received from the sensor,
   wherein prior to said receiving the update to the plurality of firmware instructions, the first set of firmware instructions is made available to the one or more processors and the second set of firmware instructions is not made available to the one or more processors,
   wherein the update to the plurality of firmware instructions makes the second set of firmware instructions available to the one or more processors.

5. The method of claim 4, wherein said determining that the handheld upgrade tool is authorized to access the physiological monitor authenticates the handheld upgrade tool for the physiological monitor.

6. The method of claim 4, further comprising identifying a tool type of the handheld upgrade tool.

7. The method of claim 6, further comprising determining that a board type of the one or more processors corresponds to the tool type of the handheld upgrade tool.

8. The method of claim 6, wherein said receiving the update to the plurality of firmware instructions is further based at least in part on said determining that a board type of the one or more processors corresponds to the tool type of the handheld upgrade tool.

9. The method of claim 6, wherein said receiving the update to the plurality of firmware instructions is further based at least in part on said determining that the board type of the one or more processors matches the tool type of the handheld upgrade tool.

10. A parameter upgrade system comprising:
   a handheld upgrade tool comprising a sensor port connector individually attachable to a sensor port of a physiological monitor in lieu of a sensor, the handheld upgrade tool configured to provide an update to a plurality of firmware instructions of the physiological monitor; and
   the physiological monitor comprising:
      the sensor port configured for attachment and communication with the sensor and further configured for attachment and communication with the handheld upgrade tool in lieu of the sensor,
      one or more processors in communication with the sensor port, and
      a data store storing the plurality of firmware instructions, the plurality of firmware instructions comprising:
         a first set of firmware instructions relating to calculation of at least one first physiological parameter in response to a sensor signal received from the sensor, wherein the first set of firmware instructions is made available to the one or more processors, and
         a second set of firmware instructions relating to calculation of at least one second physiological parameter in response to the sensor signal received from the sensor, wherein the second set of firmware instructions is not made available to the one or more processors,
   wherein the one or more processors are configured to:
      determine that the handheld upgrade tool is attached to the sensor port,
      determine that the handheld upgrade tool is authorized to access the physiological monitor; and
      based at least in part on the determination that the handheld upgrade tool is authorized to access the physiological monitor and a determination that the physiological monitor is authorized to access the handheld upgrade tool, receive the update to the plurality of firmware instructions from the handheld upgrade tool, wherein the update to the plurality of firmware instructions makes available to the one or more processors the second set of firmware instructions.

11. The parameter upgrade system of claim 10, wherein the one or more processors are configured to identify a tool type of the handheld upgrade tool.

12. The parameter upgrade system of claim 11, wherein to receive the update to the plurality of firmware instructions is further based at least in part on the determination that a board type of the one or more processors corresponds to the tool type of the handheld upgrade tool.

13. The parameter upgrade system of claim 10, wherein the one or more processors are further configured to determine that a board type of the one or more processors corresponds to a tool type of the handheld upgrade tool.

14. The parameter upgrade system of claim 10, wherein the handheld upgrade tool comprises another port connector that is different from the sensor port connector, the another port connector being configured to provide a communications path between a processor of the handheld upgrade tool and a computing device that is different from the physiological monitor.

15. The parameter upgrade system of claim 10, wherein the handheld upgrade tool is sized to fit in a palm of a hand of a user.

16. The parameter upgrade system of claim 10, wherein the sensor port connector of the handheld upgrade tool is configured to mate directly with the sensor port of the physiological monitor and provide a communications path between a processor of the handheld upgrade tool and the one or more processors of the physiological monitor.

17. The parameter upgrade system of claim 10, wherein the one or more processors are further configured to determine that a board type of the one or more processors matches a tool type of the handheld upgrade tool.

* * * * *

UNITED STATES PATENT AND TRADEMARK OFFICE
CERTIFICATE OF CORRECTION

PATENT NO. : 11,191,485 B2
APPLICATION NO. : 16/247316
DATED : December 7, 2021
INVENTOR(S) : Ammar Al-Ali It is certified that error appears in the above-identified patent and that said Letters Patent is hereby corrected as shown below:

On the Title Page

On Page 4, Column 1, (U.S. Patent Documents), Line 43: Delete "All" and insert -- Ali --.

On Page 5, Column 2, (U.S. Patent Documents), Line 41: Delete "All" and insert -- Ali --.

In the Specification

On Column 2, Line 20: Delete "RAD57™" and insert -- RAD-57™ --.

On Column 2, Line 23: Delete "RAD57™" and insert -- RAD-57™ --.

In the Claims

On Column 2, Line 16 (approx.): In Claim 1, delete "monitor" and insert -- monitor, --.

Signed and Sealed this
Twenty-sixth Day of April, 2022

Katherine Kelly Vidal
*Director of the United States Patent and Trademark Office*